(12) United States Patent
Koesling et al.

(10) Patent No.: US 9,089,137 B2
(45) Date of Patent: Jul. 28, 2015

(54) PHENYL-SUBSTITUTED KETOENOLS FOR CONTROLLING FISH PARASITES

(71) Applicant: Bayer Intellectual Property GmbH, Monheim (DE)

(72) Inventors: Jan Koesling, Bejing (CN); Reiner Fischer, Monheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/372,979

(22) PCT Filed: Jan. 22, 2013

(86) PCT No.: PCT/EP2013/051148
§ 371 (c)(1),
(2) Date: Jul. 17, 2014

(87) PCT Pub. No.: WO2013/110612
PCT Pub. Date: Aug. 1, 2013

(65) Prior Publication Data
US 2015/0005358 A1  Jan. 1, 2015

(30) Foreign Application Priority Data
Jan. 26, 2012  (EP) .................................... 12152614

(51) Int. Cl.
*A01N 43/90* (2006.01)
*A01N 43/08* (2006.01)
*A01N 43/10* (2006.01)
*A01N 43/16* (2006.01)
*A01N 43/36* (2006.01)
*A01N 43/40* (2006.01)
*A01N 43/56* (2006.01)
*A01N 43/72* (2006.01)
*A01N 43/86* (2006.01)

(52) U.S. Cl.
CPC ................. *A01N 43/90* (2013.01); *A01N 43/08* (2013.01); *A01N 43/10* (2013.01); *A01N 43/16* (2013.01); *A01N 43/36* (2013.01); *A01N 43/40* (2013.01); *A01N 43/56* (2013.01); *A01N 43/72* (2013.01); *A01N 43/86* (2013.01)

(58) Field of Classification Search
CPC ....................................... A01N 43/90
USPC ......................................... 514/409
See application file for complete search history.

(56) References Cited

U.S. PATENT DOCUMENTS

2008/0305955 A1* 12/2008 Bretschneider et al. ...... 504/225
2011/0190493 A1*  8/2011 Bretschneider et al. ...... 544/142
2011/0306499 A1* 12/2011 Bretschneider et al. ...... 504/284

* cited by examiner

*Primary Examiner* — Taofiq A Solola

(57) ABSTRACT

The present invention relates to the control of fish parasites, especially Copepodae, by means of phenyl-substituted ketoenols.

12 Claims, No Drawings

PHENYL-SUBSTITUTED KETOENOLS FOR CONTROLLING FISH PARASITES

The present invention relates to the control of fish parasites, especially Copepodae, by means of phenyl-substituted ketoenols.

Intensive fish farming suffers considerable economic losses through instances of damage to the fish that are brought about by parasites such as fish-parasitizing crustaceans such as, for example, the salmon louse or sea louse. Treatments against these parasites with metrifonate, dichlorvos, diflubenzurons, cypermethrins, deltamethrins or azamethiphos are known. These active ingredients must be used in some cases in relatively high concentrations and require a long treatment time, and in some cases, under treatments repeated without interruption, the parasites have developed resistances.

Other compounds for controlling fish parasites are known from EP-A-407 343. It is also known that, for example, agonists or antagonists of the nicotinergic acetylcholine receptors of insects can also be employed outstandingly against parasites in fish (EP-A-590 425).

It has now been found that phenyl-substituted ketoenols as well can be used for controlling parasites, especially Copepodae, in fish.

Phenyl-substituted ketoenols for controlling insects and spider mites are known from: EP-A-355 599, EP-A-415 211, JP-A-12-053 670, EP-A-377 893, EP-A-442 077, EP-A-442 073, EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140,881, WO 08/067,873, WO 08/067,910, WO 08/067,911, WO 08/138,551, WO 09/015,801, WO 09/039,975, WO 09/049,851, WO 09/115,262, PCT/EP/2009/008260. Moreover, ketal-substituted 1-H-arylpyrrolidine-2,4-diones are known from WO 99/16748, and (spiro)-ketal-substituted N-alkoxy-alkoxy-substituted aryl-pyrrolidinediones are known from JP-A-14 205 984 and Ito M. et al., Bioscience, Biotechnology and Biochemistry 67, 1230-1238, (2003). The addition of safeners to ketoenols is likewise known in principle from WO 03/013249. Moreover, WO 06/024411 discloses herbicidal compositions comprising ketoenols.

It is known that certain substituted $\Delta^3$-dihydrofuran-2-one derivatives possess herbicidal properties (cf. DE-A-4 014 420). The synthesis of the tetronic acid derivatives used as starting compounds (such as, for example, 3-(2-methylphenyl)-4-hydroxy-5-(4-fluorophenyl)-$\Delta^3$-dihydrofuran-2-one) is likewise described in DE-A-4 014 420. Similarly structured compounds, without indication of an insecticidal and/or acaricidal activity, are known from the publication Campbell et al., J. Chem. Soc., Perkin Trans. 1, 1985, (8) 1567-76. Moreover, 3-aryl-$\Delta^3$-dihydrofuranone derivatives having herbicidal, acaricidal and insecticidal properties are known from: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 07/048,545, WO 07/073,856, WO 07/096,058, WO 07/121, 868, WO 07/140,881, WO 08/067,911, WO 08/083,950, WO 09/015,801, WO 09/039,975.

Additionally, 3-aryl-$\Delta^3$-dihydrothiophen-one derivatives are known from WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/013249, WO 04/080 962, WO 04/111 042, WO 05/092897, WO 06/029799 and WO 07/096,058.

Certain phenyl-pyrone derivatives without substitution in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849), no possible usefulness as pesticides being indicated for these compounds. Phenyl-pyrone derivatives with substitution in the phenyl ring and having herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770, WO 03/013249, WO 04/080 962, WO 04/111 042, WO 05/092897, WO 06/029799 and WO 07/096,058. Furthermore, isomeric pyran-3,5-diones are described in WO 08/071,405 and WO 09/074,314.

Certain 5-phenyl-1,3-thiazine derivatives without substitution in the phenyl ring have already been disclosed (cf. E. Ziegler and E. Steiner, Monatsh. 95, 147 (1964), R. Ketcham, T. Kappe and E. Ziegler, J. Heterocycl. Chem. 10, 223 (1973)), no possible application as pesticides being indicated for these compounds. 5-Phenyl-1,3-thiazine derivatives with substitution in the phenyl ring and having herbicidal, acaricidal and insecticidal activity are described in WO 94/14 785, WO 96/2 5395, WO 96/35 664, WO 97/01 535, WO 97/02 243, WO 97/02 243, WO 97/36 868, WO 99/43649, WO 99/48869, WO 99/55673, WO 01/17972, WO 01/74770, WO 03/013249, WO 04/080 962, WO 04/111 042, WO 05/092897, WO 06/029799 and WO 07/096,058.

It is known that certain substituted 2-arylcyclopentanediones possess herbicidal, insecticidal and acaricidal properties (cf. e.g. U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO99/48869, WO 99/55673, WO 01/17972, WO 01/74770, WO 03/062244, WO 04/080962, WO 04/111042, WO 05/092897, WO 06/029799, WO 07/080,066, WO 07/096, 058, WO 09/019,005, WO 09/019,015 and EP Application Number 08166352). Moreover, similarly substituted compounds are known: 3-hydroxy-5,5-dimethyl-2-phenylcyclopent-2-ene-1-one from the publication Micklefield et al., Tetrahedron, (1992), 7519-26, and also the natural substance involutin (−)-cis-5-(3,4-dihydroxyphenyl)-3,4-dihydroxy-2-(4-hydroxyphenyl)-cyclopent-2-ene-one from the publication Edwards et al., J. Chem. Soc. S, (1967), 405-9. No insecticidal or acaricidal activity is described. Moreover, 2-(2,4,6-trimethylphenyl)-1,3-indanedione is known from the publication J. Economic Entomology, 66, (1973), 584 and from laid-open specification DE-A 2 361 084, with indication of herbicidal and acaricidal activities.

It is known that certain substituted 2-arylcyclohexanediones possess herbicidal, insecticidal and acaricidal properties (U.S. Pat. Nos. 4,175,135, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979)), WO 99/43649, WO 99/48869, WO 99/55673, WO 01/17972, WO 01/74770, WO 03/013249, WO 04/080 962, WO 04/111

042, WO 05/092897, WO 06/029799, WO 07/096,058, WO 08/071,405, WO 08/110,307, WO 08/110,308 and WO 08/145,336.

It is known that certain substituted 4-arylpyrazolidine-3,5-diones possess acaricidal, insecticidal and herbicidal properties (cf. e.g. WO 92/16 510, EP-A-508 126, WO 96/11 574, WO 96/21 652, WO 99/47525, WO 01/17 351, WO 01/17 352, WO 01/17 353, WO 01/17 972, WO 01/17 973, WO 03/028 466, WO 03/062 244, WO 04/080 962, WO 04/111 042, WO 05/005428, WO 05/016873, WO 05/092897, WO 06/029799 and WO 07/096,058).

It is known that certain tetrahydropyridones possess herbicidal properties (JP 0832530). Moreover, specific 4-hydroxytetrahydropyridones with acaricidal, insecticidal and herbicidal properties are known (JP 11152273). Additionally disclosed have been 4-hydroxytetrahydropyridones as pesticides and herbicides, in WO 01/79204 and WO 07/096,058.

It is known that certain 5,6-dihydropyrone derivatives as protease inhibitors have antiviral properties (WO 95/14012). Moreover, 4-phenyl-6-(2-phenethyl)-5,6-dihydropyrone is known from the synthesis of kavalactone derivatives (Kappe et al., Arch. Pharm. 309, 558-564 (1976)). Furthermore, 5,6-dihydropyrone derivatives as intermediates are known (White, J. D., Brenner, J. B., Deinsdale, M. J., J. Amer. Chem. Soc. 93, 281-282 (1971)). 3-Phenyl-5,6-dihydropyrone derivatives with applications in crop protection are described in WO 01/98288 and WO 07/09658.

4-Phenyl-substituted 1,2-oxazine-3,5-diones were described for the first time as herbicides in WO 01/17972. Furthermore, 4-acyl-substituted 1,2-oxazine-3,5-diones as pesticides, but especially as herbicides and growth regulators, have been described for example in EP-A-39 48 89; WO 92/07837, U.S. Pat. No. 5,728,831, and also as herbicides and pesticides in WO 03/048138.

Express reference is hereby made to the definitions and generic formulae described in these publications, and also to the individual compounds described therein. These compounds are summarized under the term cyclic ketoenols and related compounds.

These compounds can be preferably summarized under the general formula (I):

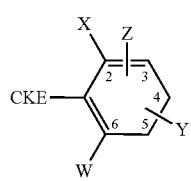
(I)

in which
W is hydrogen, alkyl, halogen, haloalkyl, alkoxy or haloalkoxy,
X is alkyl, alkenyl, alkynyl, halogen, alkoxy, haloalkyl, haloalkoxy or cyano,
Y is hydrogen, alkyl, alkoxy or halogen,
Z is hydrogen, halogen, alkyl, alkoxy, haloalkyl, haloalkoxy or optionally singly or multiply substituted phenyl,
CKE is one of the groups

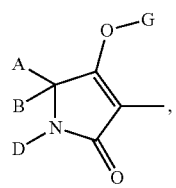
(1)

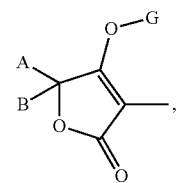
(2)

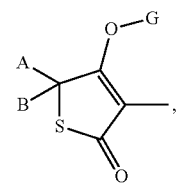
(3)

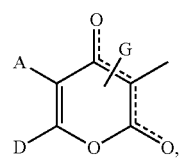
(4)

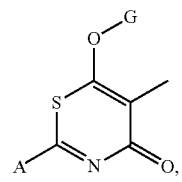
(5)

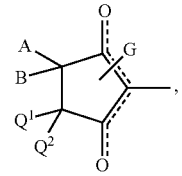
(6)

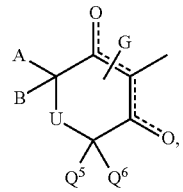
(7)

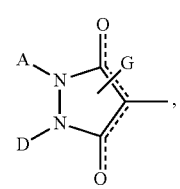
(8)

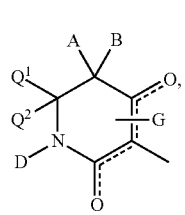
(9)

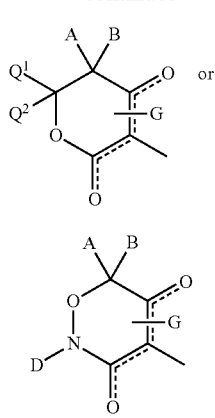

(10)

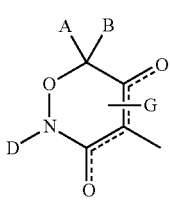

(11)

in which
U is —S—, —S(O)—, —S(O)$_2$—, —O—,

or an S=N—, S(O)=N— or

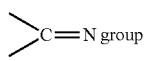

or is optionally Q$^3$ and Q$^4$-substituted C$_1$-C$_4$-alkylene which may optionally be interrupted by oxygen, A is hydrogen, or is in each case optionally halogen-substituted alkyl, alkenyl, alkoxyalkyl, alkylthioalkyl, saturated or unsaturated, optionally substituted cycloalkyl, in which optionally at least one ring atom has been replaced by a heteroatom, or is in each case optionally halogen-, alkyl-, haloalkyl-, alkoxy-, haloalkoxy-, cyano- or nitro-substituted aryl, arylalkyl or hetaryl, B is hydrogen, alkyl or alkoxyalkyl, or A and B together with the carbon atom to which they are attached are a saturated or unsaturated, unsubstituted or substituted ring system optionally containing at least one heteroatom, D is hydrogen or an optionally substituted radical from the series alkyl, alkenyl, alkynyl, alkoxyalkyl, saturated or unsaturated cycloalkyl, in which optionally one or more ring members have been replaced by heteroatoms, or is in each case optionally substituted arylalkyl, aryl, hetarylalkyl or hetaryl, or A and D together with the atoms to which they are attached are a saturated or unsaturated ring system which optionally contains at least one (when CKE=8 and 11 one further) heteroatom and which is unsubstituted or substituted in the A,D moiety, or A and Q$^1$ together are in each case optionally substituted alkanediyl or alkenediyl which may optionally be interrupted by at least one heteroatom, an

or substituted

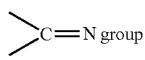

or,

B and Q$^2$ together with the atoms to which they are attached are a saturated or unsaturated ring system which optionally contains at least one heteroatom and which is unsubstituted or substituted in the B, Q$^2$ moiety, or D and Q$^1$ together with the atoms to which they are attached are a saturated or unsaturated ring system which optionally contains at least one heteroatom and which is unsubstituted or substituted in the D, Q$^1$ moiety, Q$^1$ is hydrogen, alkyl, alkoxyalkyl, optionally substituted cycloalkyl, in which optionally a methylene group has been replaced by oxygen or sulphur, or is optionally substituted phenyl, Q$^2$, Q$^4$, Q$^5$ and Q$^6$ independently of one another are hydrogen or alkyl, Q$^3$ is hydrogen, or is in each case optionally substituted alkyl, alkoxy, alkylthio, alkoxyalkyl, alkylthioalkyl, optionally substituted cycloalkyl, in which optionally one or two methylene groups have been replaced by oxygen or sulphur, or is optionally substituted phenyl, or Q$^1$ and Q$^2$ together with the carbon atom to which they are attached are an unsubstituted or substituted ring system optionally comprising a heteroatom, or Q$^3$ and Q$^4$ together with the carbon atom to which they are attached are a saturated or unsaturated, unsubstituted or substituted ring system optionally comprising at least one heteroatom, or A and Q$^3$ together with the carbon atom to which they are attached are a saturated or unsaturated, unsubstituted or substituted ring system optionally comprising at least one heteroatom, or A and Q$^5$ together with the carbon atom to which they are attached are a saturated or unsaturated, unsubstituted or substituted ring system optionally comprising at least one heteroatom, G is hydrogen (a) or is one of the groups

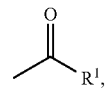 (b)

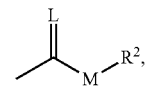 (c)

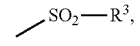 (d)

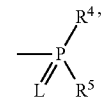 (e)

E or (f)

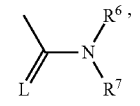 (g)

in which
E is a metal ion equivalent or an ammonium ion,
L is oxygen or sulphur,
M is oxygen or sulphur,
R$^1$ is in each case optionally halogen-substituted alkyl, alkenyl, alkoxyalkyl, alkylthioalkyl, polyalkoxyalkyl, or is optionally halogen-, alkyl- or alkoxy-substituted cycloalkyl, which may be interrupted by at least one heteroatom, or is in each case optionally substituted phenyl, phenylalkyl, hetaryl, phenoxyalkyl or hetaryloxyalkyl, $R^2$ is in each case optionally halogen-substituted alkyl, alkenyl, alkoxyalkyl, polyalkoxyalkyl, or is in each case optionally substituted cycloalkyl, phenyl or benzyl, $R^3$, $R^4$ and $R^5$ independently of one another are in each case optionally halogen-substituted alkyl, alkoxy, alkylamino, dialkylamino, alkylthio, alkenylthio, cycloalkylthio or are in each case optionally substituted phenyl, benzyl, phenoxy or phenylthio, $R^6$ and $R^7$ independently of one another are hydrogen, or are in each case optionally halogen-substituted alkyl, cycloalkyl, alkenyl, alkoxy, alkoxyalkyl, or are optionally substituted phenyl, or are optionally substituted benzyl, or together with the N atom to which they are bonded are a ring system optionally interrupted by oxygen or sulphur.

The compounds of the formula (I) may, also in dependence on the nature of the substituents, be present in the form of geometrical and/or optical isomers or isomer mixtures, in different compositions, which may optionally be separated in a conventional way. Not only the pure isomers but also the isomer mixtures can be used in compositions of the invention and can be boosted in their activity by ammonium salts or phosphonium salts according to the invention. The text below always refers, for the sake of simplicity, to compounds of the formula (I), although not only the pure compounds but also, optionally, mixtures with different fractions of isomeric compounds are meant.

Incorporation of the definitions (1) to (11) for the group CKE produces the following primary structures (I-1) to (I-11):

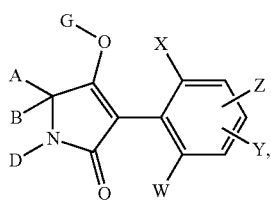
(I-1)

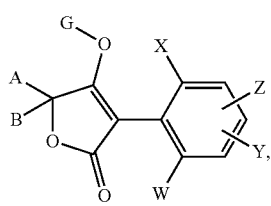
(I-2)

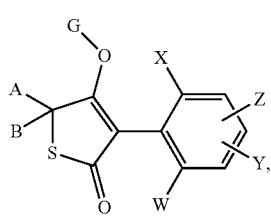
(I-3)

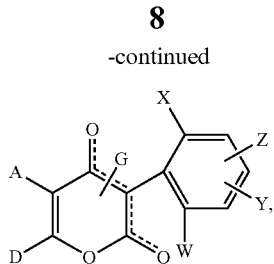
(I-4)

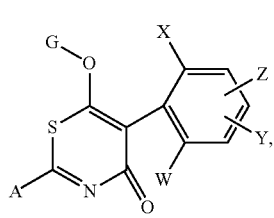
(I-5)

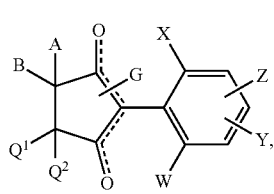
(I-6)

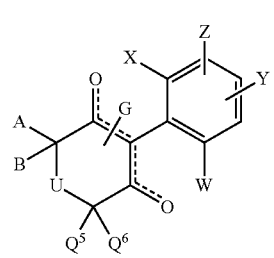
(I-7)

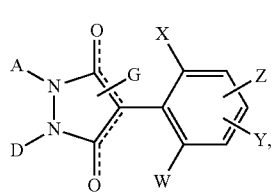
(I-8)

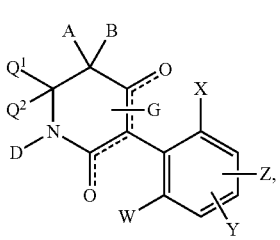
(I-9)

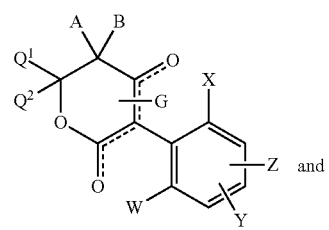
(I-10)

and

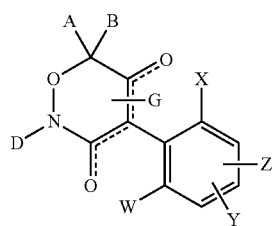
(I-11)

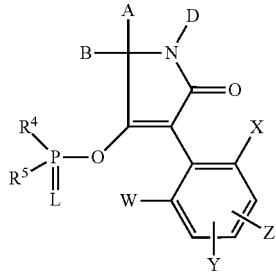
(I-1-e)

in which

A, B, D, G, $Q^1$, $Q^2$, $Q^5$, $Q^6$, U, W, X, Y and Z have the definition indicated above.

Incorporating the various definitions (a), (b), (c), (d), (e), (f) and (g) for the group G produces the following primary structures (I-1-a) to (I-1-g) when CKE is the group (1),

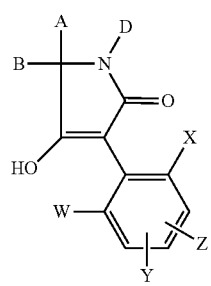
(I-1-a)

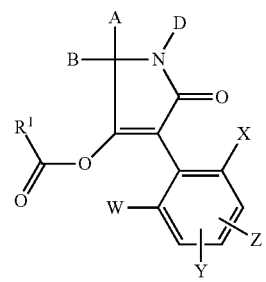
(I-1-b)

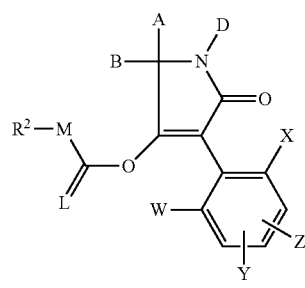
(I-1-c)

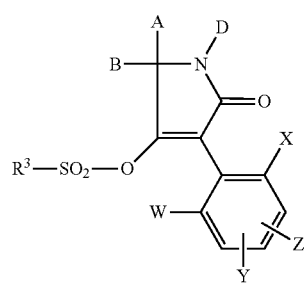
(I-1-d)

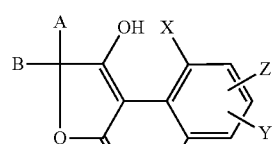
(I-1-f)

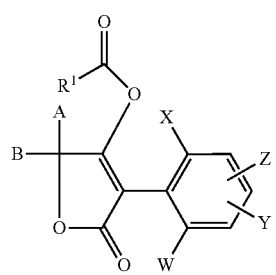
(I-1-g)

in which

A, B, D, E, L, M, W, X, Y, Z, $R^1$, $R^2$, $R^3$, $R^4$, $R^5$, $R^6$ and $R^7$ possess the definitions indicated above.

Incorporating the various definitions (a), (b), (c), (d), (e), (f) and (g) for the group G produces the following primary structures (I-2-a) to (I-2-g) when CKE is the group (2), (I-2-a)

(I-2-b)

(I-2-c)
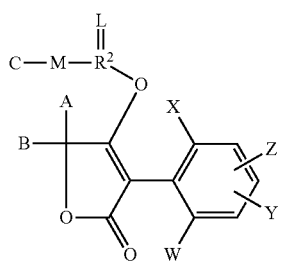
(I-2-d)
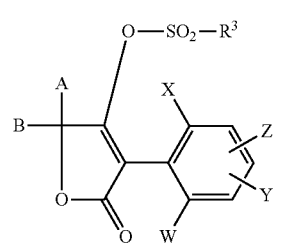
(I-2-e)
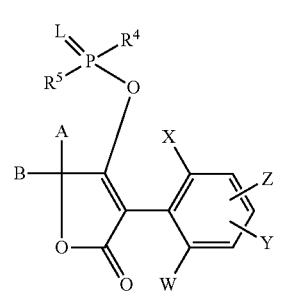
(I-2-f)
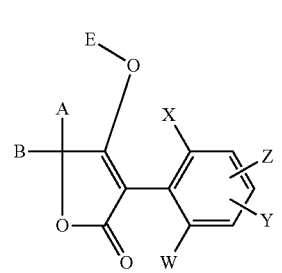
(I-2-g)
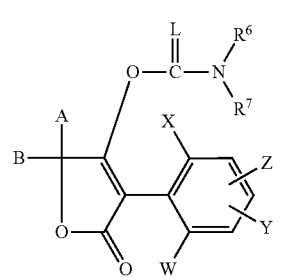
in which
A, B, E, L, M, W, X, Y, Z, $R^1$, $R^2$, $R^3$, $R^4$, $R^5$, $R^6$ and $R^7$ possess the definition indicated above.
Incorporating the various definitions (a), (b), (c), (d), (e), (f) and (g) for the group G produces the following primary structures (I-3-a) to (I-3-g) when CKE is the group (3),
(I-3-a)
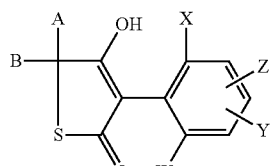
(I-3-b)
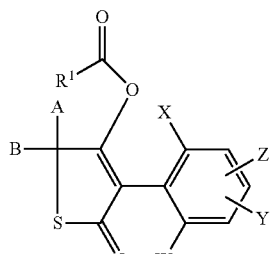
(I-3-c)
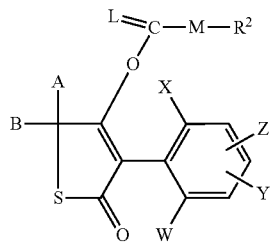
(I-3-d)
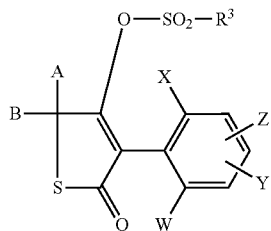
(I-3-e)
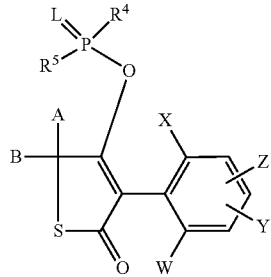
(I-3-f)
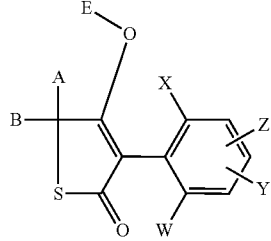

(I-3-g)

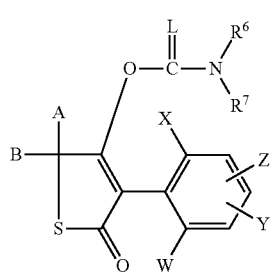

in which

A, B, E, L, M, W, X, Y, Z, $R^1$, $R^2$, $R^3$, $R^4$, $R^5$, $R^6$ and $R^7$ possess the definition indicated above.

Depending on the position of the substituent G, the compounds of the formula (I-4) may be present in the two isomeric forms of the formulae (I-4-A) and (I-4-B), (I-4-A)

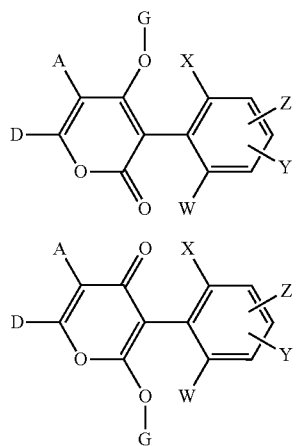

(I-4-B)

which the dashed line in the formula (I-4) is intended to express.

The compounds of the formulae (I-4-A) and (I-4-B) may be present both as mixtures and in the form of their pure isomers. Mixtures of the compounds of the formulae (I-4-A) and (I-4-B) can be separated, optionally, in a conventional way by means of physical methods, as for example by means of chromatographic methods.

In the text below, for reasons of greater ease of comprehension, only one of the possible isomers is listed in each case. This does not rule out the possibility of the compounds being present optionally in the form of the isomer mixtures or in the other isomeric form in each case.

Incorporating the various definitions (a), (b), (c), (d), (e), (f) and (g) for the group G produces the following primary structures (I-4-a) to (I-4-g) when CKE is the group (4), (I-4-a)

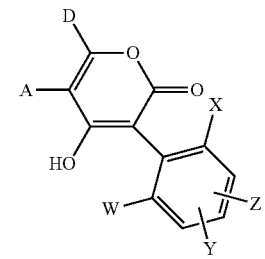

(I-4-b)

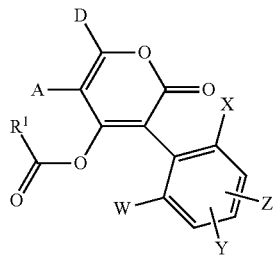

(I-4-c)

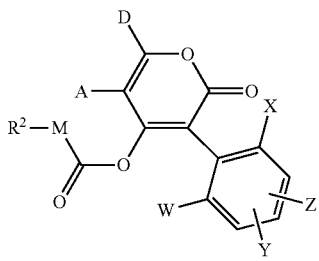

(I-4-d)

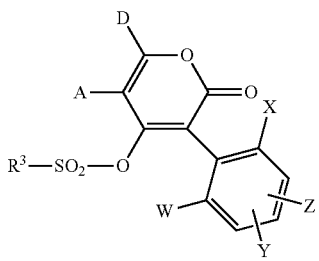

(I-4-e)

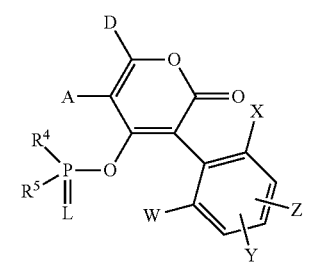

(I-4-f)

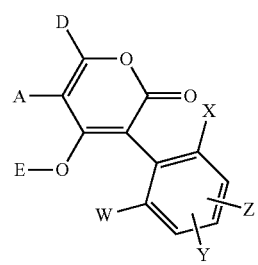

(I-4-g)

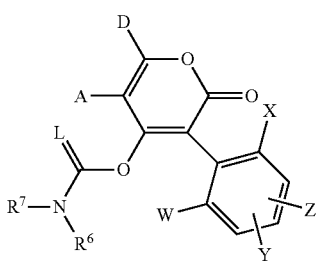

in which

A, D, E, L, M, W, X, Y, Z, $R^1$, $R^2$, $R^3$, $R^4$, $R^5$, $R^6$ and $R^7$ possess the definitions indicated above.

Incorporating the various definitions (a), (b), (c), (d), (e), (f) and (g) for the group G produces the following primary structures (I-5-a) to (I-5-g) when CKE is the group (5),

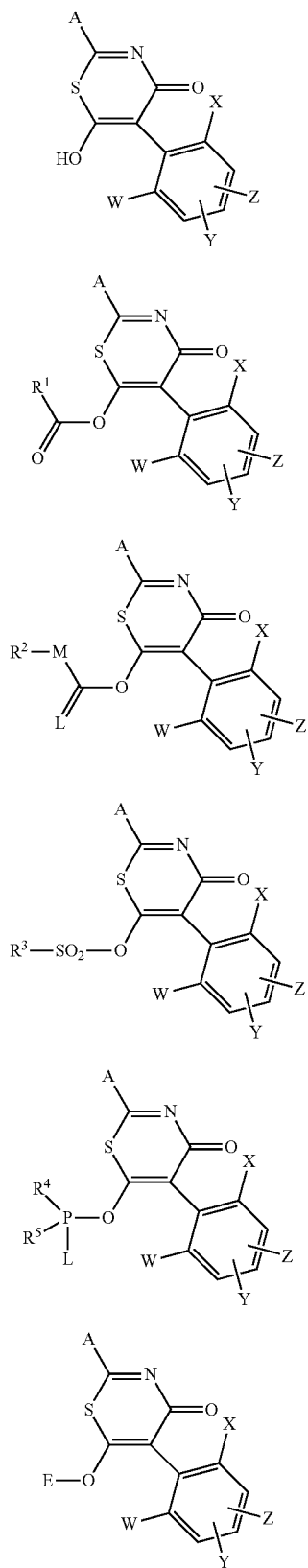

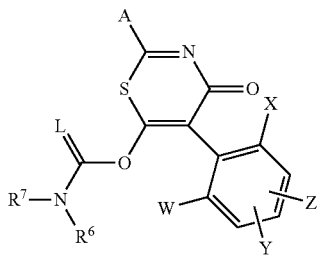

in which
A, E, L, M, W, X, Y, Z, $R^1$, $R^2$, $R^3$, $R^4$, $R^5$, $R^6$ and $R^7$ possess the definitions indicated above.

Depending on the position of the substituent G, the compounds of the formula (I-6) may be present in the two isomeric forms of the formulae (I-6-A) and (I-6-B),

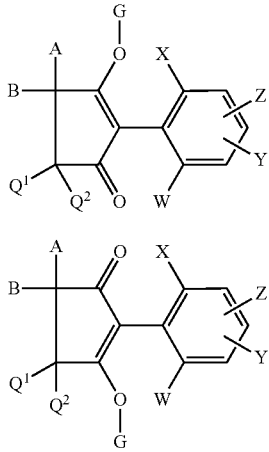

which the dashed line in the formula (I-6) is intended to express.

The compounds of the formulae (I-6-A) and (I-6-B) may be present both as mixtures and in the form of their pure isomers. Mixtures of the compounds of the formulae (I-6-A) and (I-6-B) can be separated, optionally, by means of physical methods, as for example by means of chromatographic methods.

In the text below, for reasons of greater ease of comprehension, only one of the possible isomers is listed in each case. This does not rule out the possibility of the compounds being present optionally in the form of the isomer mixtures or in the other isomeric form in each case.

Incorporating the various definitions (a), (b), (c), (d), (e), (f) and (g) for the group G produces the following primary structures (I-6-a) to (I-6-g) when CKE is the group (6),

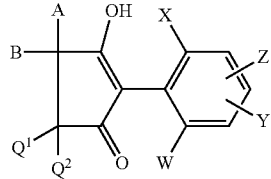

-continued

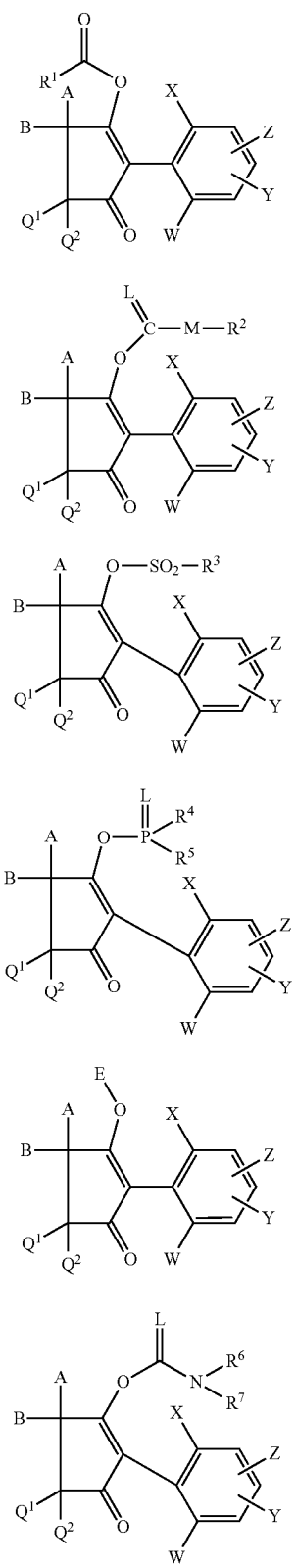

in which

A, B, Q$^1$, Q$^2$, E, L, M, W, X, Y, Z, R$^1$, R$^2$, R$^3$, R$^4$, R$^5$, R$^6$ and R$^7$ possess the definitions indicated above.

Depending on the position of the substituent G, the compounds of the formula (I-7) may be present in the two isomeric forms of the formulae (I-7-A) and (I-7-B), which the dashed line in the formula (I-7) is intended to express:

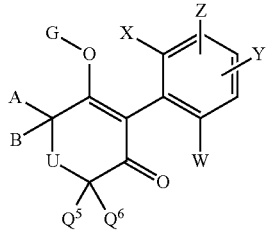
(I-7-A)

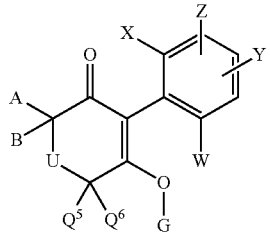
(I-7-B)

The compounds of the formulae (I-7-A) and (I-7-B) may be present both as mixtures and in the form of their pure isomers. Mixtures of the compounds of the formulae (I-7-A) and (I-7-B) can be separated, optionally, by means of physical methods, as for example by means of chromatographic methods.

In the text below, for reasons of greater ease of comprehension, only one of the possible isomers is listed in each case. This does not rule out the possibility of the compound in question being present optionally in the form of the isomer mixture or in the other isomeric form in each case.

Incorporating the various definitions (a), (b), (c), (d), (e), (f) and (g) for the group G produces the following primary structures (I-7-a) to (I-7-g) when CKE is the group (7),

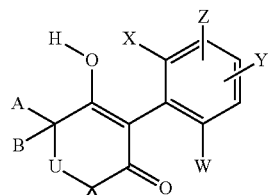
(I-7-a)

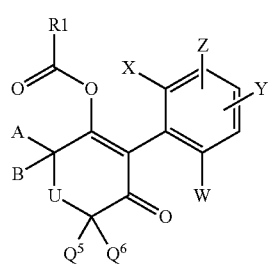
(I-7-b)

-continued

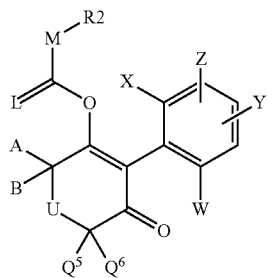
(I-7-c)

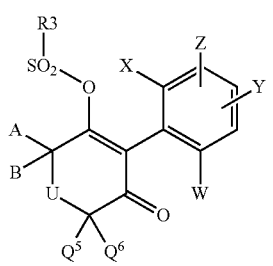
(I-7-d)

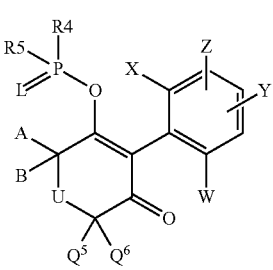
(I-7-e)

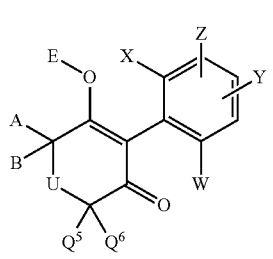
(I-7-f)

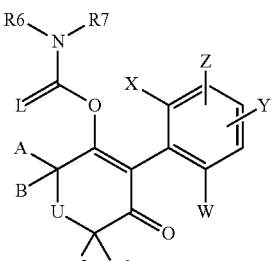
(I-7-g)

in which

A, B, E, L, M, $Q^5$, $Q^6$, U, W, X, Y, Z, $R^1$, $R^2$, $R^3$, $R^4$, $R^5$, $R^6$ and $R^7$ possess the definitions indicated above.

Depending on the position of the substituent G, the compounds of the formula (I-8) may be present in the two isomeric formulae (I-8-A) and (I-8-B),

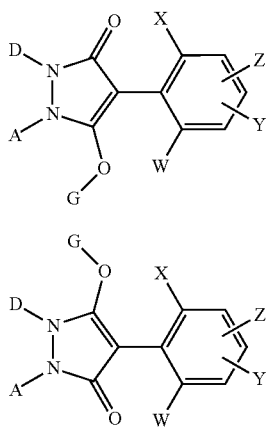
(I-8-A)

(I-8-B)

which the dashed line in the formula (I-8) is intended to express.

The compounds of the formulae (I-8-A) and (I-8-B) may be present both as mixtures and in the form of their pure isomers. Mixtures of the compounds of the formulae (I-8-A) and (I-8-B) can be separated, optionally, in a conventional way by means of physical methods, as for example by means of chromatographic methods.

In the text below, for reasons of greater ease of comprehension, only one of the possible isomers is listed in each case. This does not rule out the possibility of the compounds being present optionally in the form of the isomer mixtures or in the other isomeric form in each case.

Incorporating the various definitions (a), (b), (c), (d), (e), (f) and (g) for the group G produces the following primary structures (I-8-a) to (I-8-g) when CKE is the group (8),

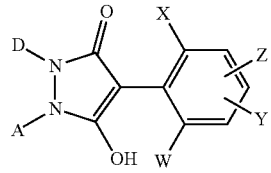
(I-8-a)

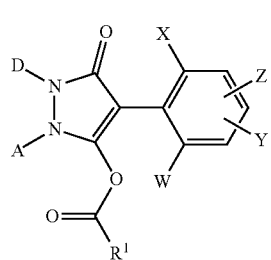
(I-8-b)

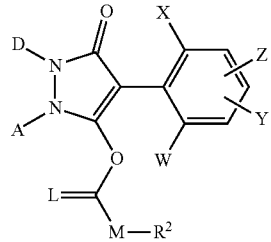
(I-8-c)

(I-8-d)
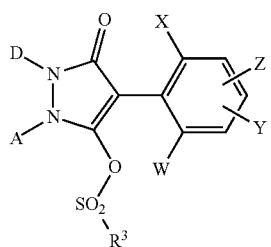

(I-8-e)
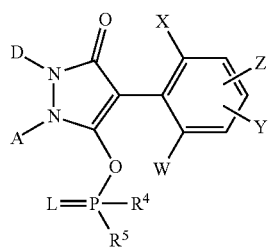

(I-8-f)
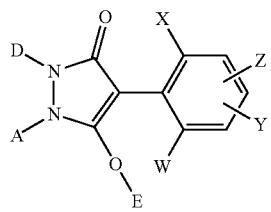

(I-8-g)
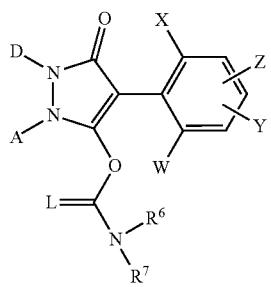

in which

A, D, E, L, M, W, X, Y, Z, $R^1$, $R^2$, $R^3$, $R^4$, $R^5$, $R^6$ and $R^7$ possess the definitions indicated above.

Depending on the position of the substituent G, the compounds of the formula (I-9) may be present in the two isomeric forms of the formulae (I-9-A) and (I-9-B), which the dashed line in the formula (I-9) is intended to express:

(I-9-A)
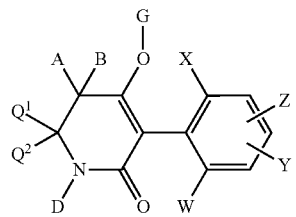

(I-9-B)
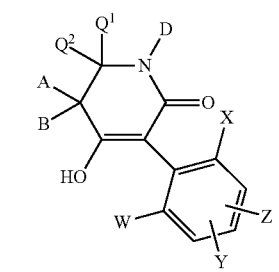

The compounds of the formulae (I-9-A) and (I-9-B) may be present both as mixtures and in the form of their pure isomers. Mixtures of the compounds of the formulae (I-9-A) and (I-9-B) can be separated, optionally, in a conventional way by means of physical methods, as for example by means of chromatographic methods.

In the text below, for reasons of greater ease of comprehension, only one of the possible isomers is listed in each case. This does not rule out the possibility of the compounds being present optionally in the form of the isomer mixtures or in the other isomeric form in each case.

Incorporating the various definitions (a), (b), (c), (d), (e), (f) and (g) for the group G produces the following primary structures (I-9-a) to (I-9-g) when CKE is the group (9), (I-9-a)
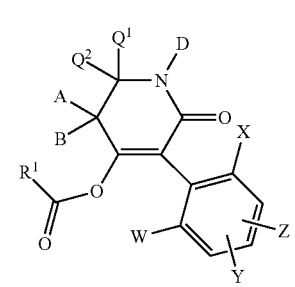

(I-9-b)
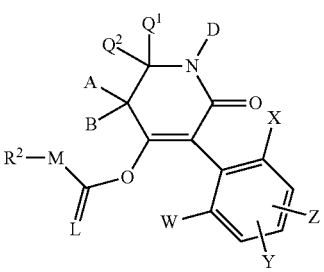

(I-9-c)

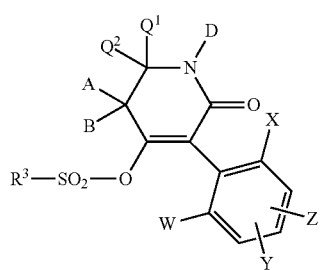
(I-9-d)

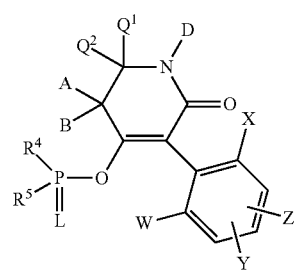
(I-9-e)

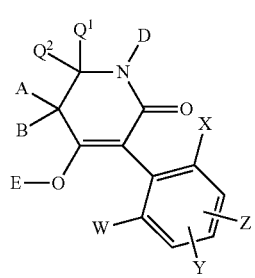
(I-9-f)

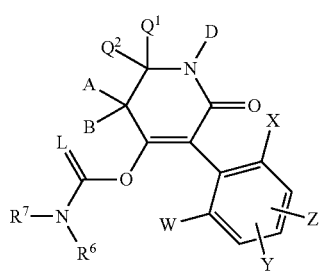
(I-9-g)

in which

A, B, D, E, L, M, $Q^1$, $Q^2$, W, X, Y, Z, $R^1$, $R^2$, $R^3$, $R^4$, $R^5$, $R^6$ and $R^7$ possess the definitions indicated above.

Depending on the position of the substituent G, the compounds of the formula (I-10) may be present in the two isomeric forms of the formulae (I-10-A) and (I-10-B),

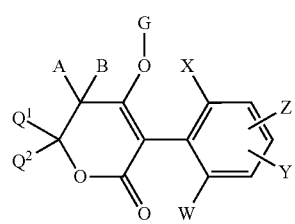
(I-10-A)

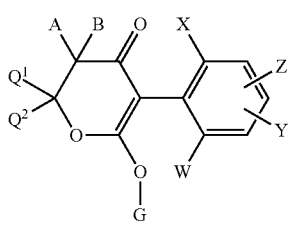
(I-10-B)

which the dashed line in the formula (I-10) is intended to express.

The compounds of the formulae (I-10-A) and (I-10-B) may be present both as mixtures and in the form of their pure isomers. Mixtures of the compounds of the formulae (I-10-A) and (I-10-B) can be separated, optionally, in a conventional way by means of physical methods, as for example by means of chromatographic methods.

In the text below, for reasons of greater ease of comprehension, only one of the possible isomers is listed in each case. This does not rule out the possibility of the compounds being present optionally in the form of the isomer mixtures or in the other isomeric form in each case.

Incorporating the various definitions (a), (b), (c), (d), (e), (f) and (g) for the group G produces the following primary structures (I-10-a) to (I-10-g) when CKE is the group (10),

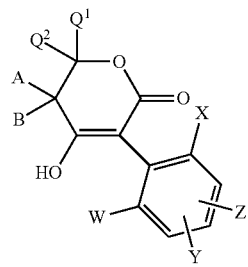
(I-10-a)

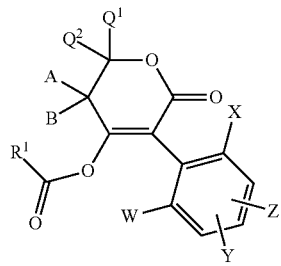
(I-10-b)

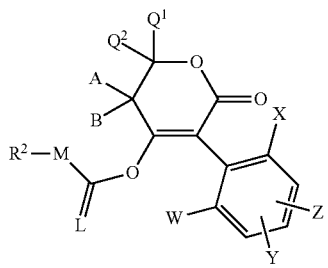
(I-10-c)

-continued (I-10-d)
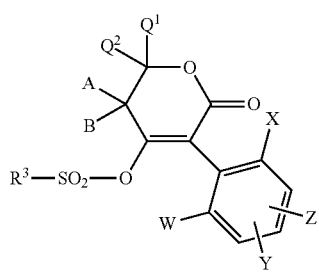

(I-10-e)
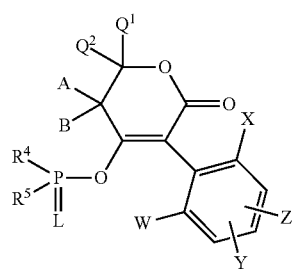

(I-10-f)
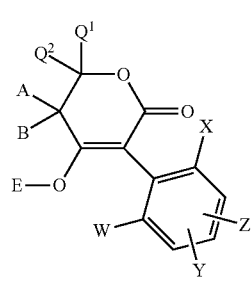

(I-10-g)
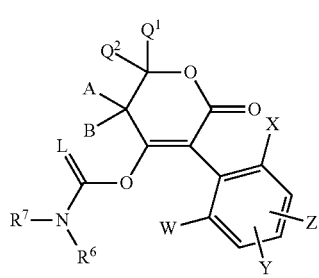

in which

A, B, E, L, M, $Q^1$, $Q^2$, W, X, Y, Z, $R^1$, $R^2$, $R^3$, $R^4$, $R^5$, $R^6$ and $R^7$ possess the definitions indicated above.

Depending on the position of the substituent G, the compounds of the formula (I-11) may be present in the two isomeric forms of the formulae (I-11-A) and (I-11-B), which the dashed line in the formula (I-11) is intended to express.

(I-11-A)
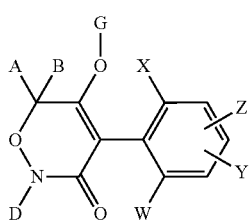

(I-11-B)
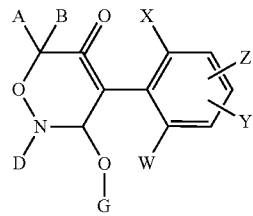

The compounds of the formulae (I-11-A) and (I-11-B) may be present both as mixtures and in the form of their pure isomers. Mixtures of the compounds of the formulae (I-11-A) and (I-11-B) can be separated, optionally, in a conventional way by means of physical methods, as for example by means of chromatographic methods.

In the text below, for reasons of greater ease of comprehension, only one of the possible isomers is listed in each case. This does not rule out the possibility of the compounds being present optionally in the form of the isomer mixtures or in the other isomeric form in each case.

Incorporating the various definitions (a), (b), (c), (d), (e), (f) and (g) for the group G produces the following primary structures (I-11-a) to (I-11-g) when CKE is the group (11), (I-11-a)
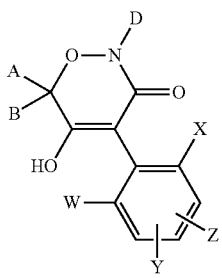

(I-11-b)
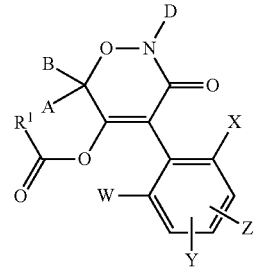

(I-11-c)
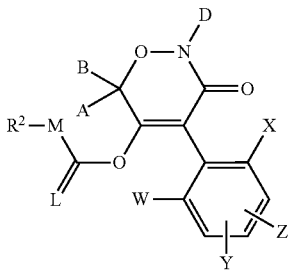

-continued

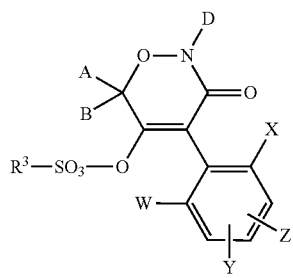
(I-11-d)

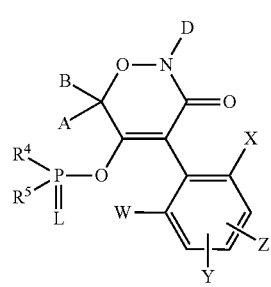
(I-11-e)

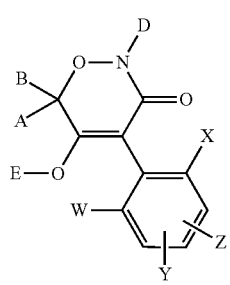
(I-11-f)

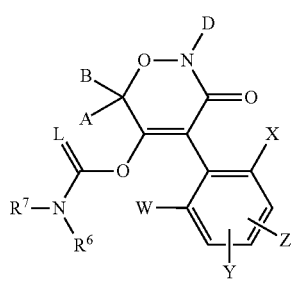
(I-11-g)

in which

A, B, D, E, L, M, W, X, Y, Z, $R^1$, $R^2$, $R^3$, $R^4$, $R^5$, $R^6$ and $R^7$ possess the definitions indicated above.

A general definition of the compounds is provided by the formula (I). Preferred substituents and ranges of the radicals set out in the formulae referred to above and below are elucidated in the following text:

W is preferably hydrogen, $C_1$-$C_6$-alkyl, halogen, $C_1$-$C_6$-alkoxy, $C_1$-$C_4$-haloalkyl or $C_1$-$C_4$-haloalkoxy, X is preferably halogen, $C_1$-$C_6$-alkyl, $C_2$-$C_6$-alkenyl, $C_2$-$C_6$-alkynyl, $C_1$-$C_6$-alkoxy, $C_1$-$C_4$-haloalkyl, $C_1$-$C_4$-haloalkoxy or cyano, Y is preferably hydrogen, halogen, $C_1$-$C_6$-alkyl, or $C_1$-$C_6$-alkoxy, Z is preferably hydrogen, $C_1$-$C_4$-alkyl, halogen or a radical

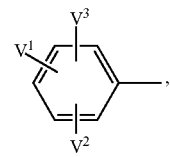

$V^1$ is preferably hydrogen, halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro or cyano, $V^2$ is preferably hydrogen, halogen, $C_1$-$C_6$-alkyl or $C_1$-$C_6$-alkoxy, $V^3$ is preferably hydrogen or halogen, CKE is preferably one of the groups

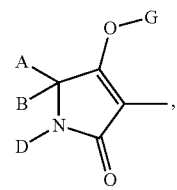
(1)

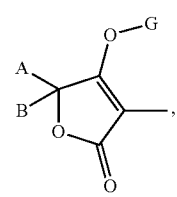
(2)

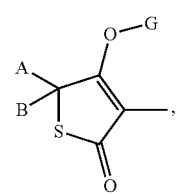
(3)

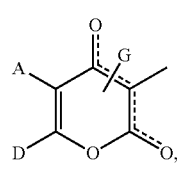
(4)

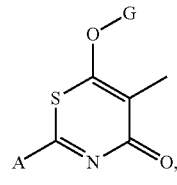
(5)

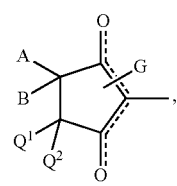
(6)

-continued

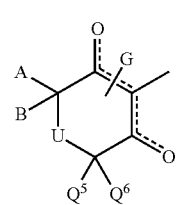
(7)

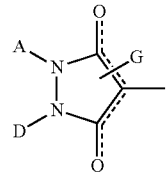
(8)

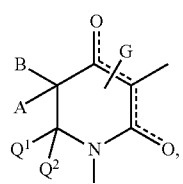
(9)

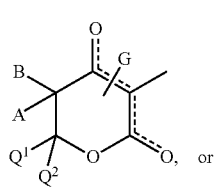
(10)

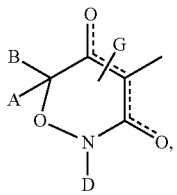
(11)

U is preferably —S—, —S(O)—, —S(O)$_2$—, —O—,

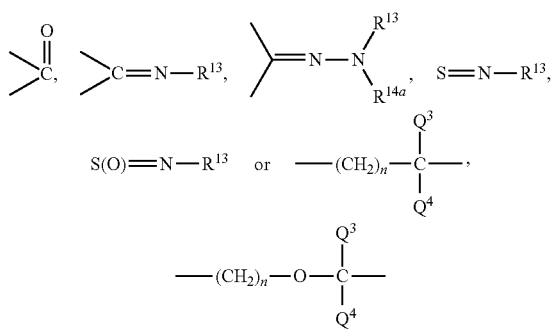

in which n is the number 0, 1 or 2,

A is preferably hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl, in which optionally one or two ring members not directly adjacent have been replaced by oxygen and/or sulphur, or is in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, naphthyl, hetaryl having 5 to 6 ring atoms (for example, furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B is preferably hydrogen, $C_1$-$C_{12}$-alkyl or $C_1$-$C_8$-alkoxy-$C_1$-$C_6$-alkyl or A, B and the carbon atom to which they are bonded are preferably saturated $C_3$-$C_{10}$-cycloalkyl or unsaturated $C_5$-$C_{10}$-cycloalkyl, in which optionally one ring member has been replaced by nitrogen, oxygen or sulphur and which are optionally singly or doubly substituted by $C_1$-$C_8$-alkyl, $C_1$-$C_8$-alkoxy, $C_3$-$C_8$-alkenyloxy, $C_1$-$C_6$-alkoxy-$C_1$-$C_6$-alkyl, $C_3$-$C_6$-cycloalkyl-$C_1$-$C_2$-alkoxy, $C_3$-$C_{10}$-cycloalkyl, $C_1$-$C_8$-haloalkyl, $C_2$-$C_6$-haloalkoxy, $C_1$-$C_6$-alkoxy-$C_1$-$C_4$-alkoxy, the aforementioned radicals also being suitable as N substituents, or A, B and the carbon atom to which they are bonded are preferably $C_3$-$C_6$-cycloalkyl which is substituted by an alkylenedithioyl or by an alkylenedioxyl or by an alkylenediyl group which is optionally $C_1$-$C_4$-alkyl-substituted and which optionally comprises one or two oxygen and/or sulphur atoms that are not directly adjacent, and which, with the carbon atom to which it is bonded, forms a further five- to eight-membered ring, or A, B and the carbon atom to which they are bonded are preferably $C_3$-$C_8$-cycloalkyl or $C_5$-$C_8$-cycloalkenyl, in which two substituents together with the carbon atoms to which they are bonded are in each case optionally $C_1$-$C_6$-alkyl, $C_1$-$C_6$-alkoxy- or halogen-substituted $C_2$-$C_6$-alkanediyl, $C_2$-$C_6$-alkenediyl or $C_4$-$C_6$-alkanedienediyl, in which optionally one methylene group has been replaced by oxygen or sulphur, D is preferably hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_1$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl, in which optionally one ring member has been replaced by oxygen or sulphur, or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl), or A and D are together preferably in each case optionally substituted $C_3$-$C_6$-alkanediyl or $C_3$-$C_6$-alkenediyl, in which optionally one methylene group has been replaced by one carbonyl group, oxygen or sulphur, and where suitable substituents in each case are as follows:
halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl moiety, $C_3$-$C_6$-alkenediyl moiety or a butadienyl moiety which is optionally substituted by $C_1$-$C_6$-alkyl or in which optionally two adjacent substituents, with the carbon atoms to which they are bonded, form a further saturated or unsaturated ring system having 5 or 6 ring atoms (in the case of the compound of the formula (I-1), A and D then, together with the atoms to which they are bonded, are the groups AD-1 to AD-10 specified later on below), which may contain oxygen or sulphur, or in which optionally one of the following groups

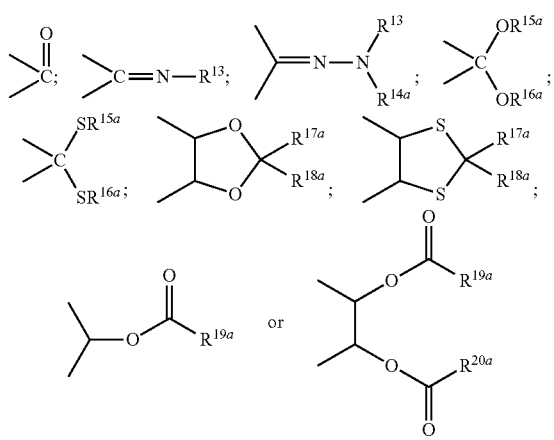

is present, or

A and $Q^1$ preferably together with the carbon atoms to which they are bonded are $C_3$-$C_6$-alkanediyl or $C_4$-$C_6$-alkenediyl, each of which is optionally substituted singly or doubly and identically or differently by halogen, hydroxyl, by in each case optionally singly to triply, identically or differerently halogen-substituted $C_1$-$C_{10}$-alkyl, $C_1$-$C_8$-alkenyl, $C_1$-$C_6$-alkoxy, $C_1$-$C_6$-alkylthio, $C_3$-$C_7$-cycloalkyl or by in each case optionally singly to triply, identically or differently halogen-, $C_1$-$C_6$-alkyl- or $C_1$-$C_6$-alkoxy-substituted benzyloxy or phenyl, and which further optionally comprises one of the following groups

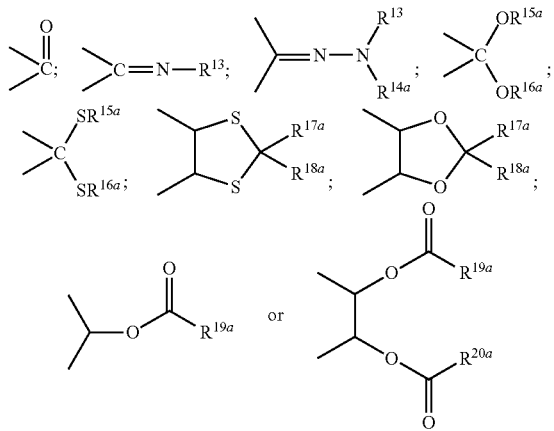

or is bridged by a $C_1$-$C_2$-alkanediyl group or by an oxygen atom, or

B and $Q^2$ together preferably are optionally $C_1$-$C_2$-alkyl-substituted $C_1$-$C_3$-alkanediyl, which may optionally be interrupted by oxygen, or D and $Q^1$ together preferably are optionally singly or doubly, identically or differently $C_1$-$C_4$-alkyl-, $C_1$-$C_4$-alkoxy-substituted $C_3$-$C_6$-alkanediyl, or $Q^1$ is preferably hydrogen, $C_1$-$C_6$-alkyl, $C_1$-$C_6$-alkoxy-$C_1$-$C_2$-alkyl, optionally fluorine-, chlorine-, $C_1$-$C_4$-alkyl-, $C_1$-$C_2$-haloalkyl- or $C_1$-$C_4$-alkoxy-substituted $C_3$-$C_8$-cycloalkyl, in which optionally one methylene group is replaced by oxygen or sulphur, or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, $Q^2$, $Q^4$, $Q^5$ and $Q^6$ independently of one another are preferably hydrogen or $C_1$-$C_4$-alkyl, $Q^3$ is preferably hydrogen, $C_1$-$C_6$-alkyl, $C_1$-$C_6$-alkoxy, $C_1$-$C_6$-alkylthio, $C_1$-$C_6$-alkoxy-$C_1$-$C_2$-alkyl, $C_1$-$C_6$-alkylthio-$C_1$-$C_2$-alkyl, optionally $C_1$-$C_4$-alkyl- or $C_1$-$C_4$-alkoxy-substituted $C_3$-$C_8$-cycloalkyl, in which optionally one or two methylene groups have been replaced by oxygen or sulphur, or optionally halogen-, $C_1$-$C_4$-alkyl-, $C_1$-$C_4$-alkoxy-, $C_1$-$C_2$-haloalkyl-, $C_1$-$C_2$-haloalkoxy-, cyano- or nitro-substituted phenyl, or $Q^1$ and $Q^2$ preferably with the carbon atom to which they are bonded are an optionally $C_1$-$C_6$-alkyl-, $C_1$-$C_6$-alkoxy- or $C_1$-$C_2$-haloalkyl-substituted $C_3$-$C_7$ ring, in which optionally one ring member has been replaced by oxygen or sulphur, $Q^3$ and $Q^4$ preferably together with the carbon atom to which they are bonded are an optionally $C_1$-$C_4$-alkyl-, $C_1$-$C_4$-alkoxy- or $C_1$-$C_2$-haloalkyl-substituted saturated or unsaturated $C_3$-$C_7$ ring, in which optionally one or two ring members have been replaced by oxygen or sulphur, A and $Q^3$ preferably together with the carbon atoms to which they are bonded are an optionally saturated or unsaturated $C_1$-$C_4$-alkyl-, $C_1$-$C_4$-alkoxy- or $C_1$-$C_2$-haloalkyl-substituted $C_3$-$C_7$ ring, in which optionally one or two ring members have been replaced by oxygen or sulphur, A and $Q^5$ preferably together with the carbon atoms to which they are bonded are an optionally saturated or unsaturated $C_1$-$C_4$-alkyl-, $C_1$-$C_4$-alkoxy- or $C_1$-$C_2$-haloalkyl-substituted $C_3$-$C_7$ ring, in which optionally one ring member has been replaced by oxygen or sulphur, G is preferably hydrogen (a) or is one of the groups

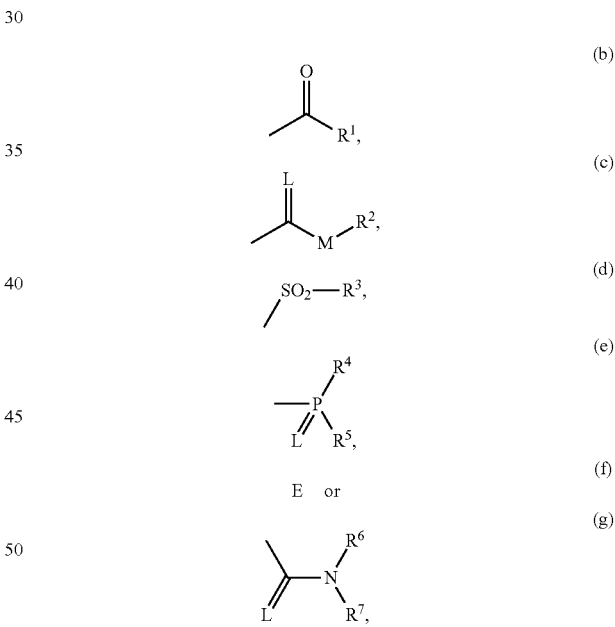

more particularly is (a), (b), (c) or (g)

in which

E is a metal ion equivalent or an ammonium ion,

L is oxygen or sulphur and

M is oxygen or sulphur.

$R^1$ preferably is in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl, in which optionally one or more (preferably not more than two) ring members not directly adjacent have been replaced by oxygen and/or sulphur, is optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, or is optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, is optionally halogen- or $C_1$-$C_6$-alkyl-substituted 5- or 6-membered hetaryl (for example pyrazolyl, thiazolyl, pyridyl, pyrimidyl, furanyl or thienyl), or is optionally halogen- or $C_1$-$C_6$-alkyl-substituted phenoxy-$C_1$-$C_6$-alkyl or is optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably is in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, or is optionally halogen-, $C_1$-$C_6$-alkyl- or $C_1$-$C_6$-alkoxy-substituted $C_3$-$C_8$-cycloalkyl or is in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably is optionally halogen-substituted $C_1$-$C_8$-alkyl or is in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ preferably independently of one another are in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or are in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably are hydrogen, or are in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, or are optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together are an optionally $C_1$-$C_4$-alkyl-substituted $C_3$-$C_6$-alkylene radical in which optionally one carbon atom has been replaced by oxygen or sulphur, $R^{13}$ preferably is hydrogen, or is in each case optionally halogen-substituted $C_1$-$C_8$-alkyl or $C_1$-$C_8$-alkoxy (only in the case of the C=N—$R^{13}$ group), or is optionally halogen-, $C_1$-$C_4$-alkyl- or $C_1$-$C_4$-alkoxy-substituted $C_3$-$C_8$-cycloalkyl, in which optionally one methylene group has been replaced by oxygen or sulphur, or is in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl, hetaryl-$C_1$-$C_4$-alkyl, or only in the case of the C=N—$R^{13}$ group is phenyl-$C_1$-$C_4$-alkoxy or hetaryl-$C_1$-$C_4$-alkoxy, $R^{14a}$ preferably is hydrogen or $C_1$-$C_8$-alkyl or $R^{13}$ and $R^{14a}$ together preferably are optionally $C_1$-$C_4$-alkyl-substituted $C_4$-$C_6$-alkanediyl, which may optionally be interrupted by oxygen or sulphur, $R^{15a}$ and $R^{16a}$ are identical or different and preferably are $C_1$-$C_6$-alkyl or $R^{15a}$ and $R^{16a}$ together preferably are a $C_2$-$C_4$-alkanediyl radical or $C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17a}$ and $R^{18a}$ independently of one another preferably are hydrogen, or are optionally halogen-substituted $C_1$-$C_8$-alkyl or are optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17a}$ and $R^{18a}$ together with the carbon atom to which they are bonded preferably are a carbonyl group or are optionally halogen-, $C_1$-$C_4$-alkyl- or $C_1$-$C_4$-alkoxy-substituted $C_5$-$C_7$-cycloalkyl, in which optionally one methylene group has been replaced by oxygen or sulphur, $R^{19a}$ and $R^{20a}$ independently of one another preferably are $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions stated as being preferred, halogen is fluorine, chlorine, bromine and iodine, more particularly fluorine, chlorine and bromine.

W more preferably is hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, X more preferably is chlorine, bromine, iodine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl, $C_1$-$C_2$-haloalkoxy or cyano, Y more preferably is hydrogen, methyl, ethyl, fluorine, chlorine, bromine, iodine, methoxy or ethoxy, Z more preferably is hydrogen, methyl, ethyl, chlorine, bromine or the radical

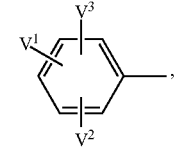

$V^1$ more preferably is hydrogen, fluorine, chorine, bromine, $C_1$-$C_6$-alkyl or $C_1$-$C_4$-alkoxy, $C_1$-$C_2$-haloalkyl or $C_1$-$C_2$-haloalkoxy, $V^2$ more preferably is hydrogen, fluorine, chlorine, bromine, $C_1$-$C_4$-alkyl or $C_1$-$C_4$-alkoxy, $V^3$ more preferably is hydrogen, fluorine or chlorine, CKE more preferably is one of the groups (1)

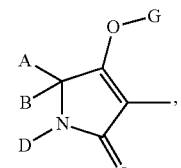

(2)

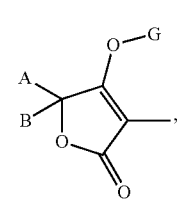

A more preferably is methyl, ethyl, propyl, isopropyl, butyl, isobutyl, sec-butyl, tert-butyl, cyclopropyl, cyclopentyl or cyclohexyl, B more preferably is hydrogen, methyl or ethyl, A, B and the carbon atom to which they are bonded more preferably are saturated or unsaturated $C_3$-$C_7$-cycloalkyl in which optionally one ring member has been replaced by oxygen or sulphur and which is optionally singly to doubly substituted by $C_1$-$C_6$-alkyl, $C_1$-$C_6$-alkoxy, $C_1$-$C_4$-alkoxy- C₁-C₂-alkyl, trifluoromethyl, C₁-C₃-alkoxy-C₁-C₃-alkoxy or C₃-C₆-cycloalkylmethoxy, or A, B and the carbon atom to which they are bonded more preferably are C₅-C₆-cycloalkyl which is substituted by an alkylenedithiol or an alkylenedioxyl or an alkylenediyl group which is optionally substituted by methyl, ethyl or methoxymethyl and which optionally comprises one or two oxygen or sulphur atoms not directly adjacent, and which, with the carbon atom to which it is attached, forms a further five- or six-membered ring, or G more preferably is hydrogen (a) or is one of the groups

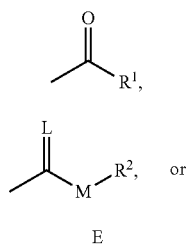

in which

E is a metal ion equivalent or an ammonium ion,

L is oxygen or sulphur and

M is oxygen or sulphur,

R¹ more preferably is in each case optionally singly to triply fluorine- or chlorine-substituted C₁-C₈-alkyl, C₂-C₈-alkenyl, C₁-C₄-alkoxy-C₁-C₂-alkyl, C₁-C₄-alkylthio-C₁-C₂-alkyl or optionally singly to doubly fluorine-, chlorine-, C₁-C₂-alkyl- or C₁-C₂-alkoxy-substituted C₃-C₆-cycloalkyl, in which optionally one or two ring members not directly adjacent have been replaced by oxygen, or is optionally singly to doubly fluorine-, chlorine-, bromine-, cyano-, nitro-, C₁-C₄-alkyl-, C₁-C₄-alkoxy-, C₁-C₂-haloalkyl- or C₁-C₂-haloalkoxy-substituted phenyl, R² more preferably is in each case optionally singly to triply fluorine-substituted C₁-C₈-alkyl, C₂-C₈-alkenyl or C₁-C₄-alkoxy-C₂-C₄-alkyl, or is optionally singly C₁-C₂-alkyl- or C₁-C₂-alkoxy-substituted C₃-C₆-cycloalkyl, or is in each case optionally singly to doubly fluorine-, chlorine-, bromine-, cyano-, nitro-, C₁-C₄-alkyl-, C₁-C₃-alkoxy-, trifluoromethyl- or trifluoromethoxy-substituted phenyl or benzyl.

In the radical definitions stated as being particularly preferred, halogen or halo is fluorine, chlorine and bromine, more particularly fluorine and chlorine.

CKE very preferably is the group

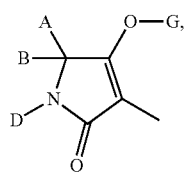

W very preferably is hydrogen or methyl,

X very preferably is chlorine, bromine, methyl, ethyl methoxy, ethoxy, trifluoromethyl, difluoromethoxy or trifluoromethoxy, Y very preferably is hydrogen, methyl, chlorine, bromine or trifluoromethoxy, Z very preferably is hydrogen or the radical

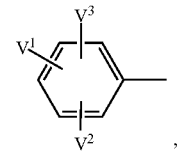

V¹ very preferably is hydrogen, fluorine, chlorine, methyl, ethyl, methoxy, ethoxy, trifluoromethyl or trifluoromethoxy, V² very preferably is hydrogen, fluorine, chlorine, methyl or methoxy, V³ very preferably is hydrogen or fluorine, A, B and the carbon atom to which they are bonded very preferably are saturated C₅-C₆-cycloalkyl in which optionally one ring member has been replaced by oxygen or sulphur and which is optionally singly or doubly substituted by methyl, ethyl, propyl, methoxy, ethoxy, propoxy, butoxy, methoxymethyl, ethoxymethyl, propoxymethyl, methoxyethyl, ethoxyethyl, trifluoromethyl, methoxyethoxy, ethoxyethoxy or cyclopropylmethoxy, or A, B and the carbon atom to which they are bonded very preferably are C₆-cycloalkyl which is substituted by a C₄-C₅-alkylenedioxyl group, which with the carbon atom to which it is bonded forms an optionally in each case singly to doubly methyl-substituted 5-membered or 6-membered ring ketal, G very preferably is hydrogen (a) or is one of the groups

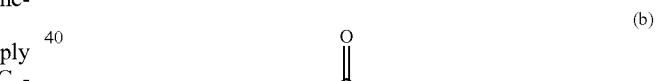

in which

L is oxygen or sulphur,

M is oxygen or sulphur and

E is a metal ion equivalent or an ammonium ion,

R¹ very preferably is in each case optionally singly fluorine- or chlorine-substituted C₁-C₆-alkyl, C₂-C₆-alkenyl, C₁-C₂-alkoxy-C₁-alkyl, C₁-C₂-alkylthio-C₁-alkyl or in each case optionally singly fluorine-, chlorine-, methyl- or methoxy-substituted cyclopropyl or cyclohexyl, is optionally singly fluorine-, chlorine-, bromine-, cyano-, nitro-, methyl-, methoxy-, trifluoromethyl- or trifluoromethoxy-substituted phenyl, R² very preferably is in each case optionally singly fluorine-substituted C₁-C₈-alkyl, C₂-C₆-alkenyl or C₁-C₄-alkoxy-C₂-C₃-alkyl, phenyl or benzyl, CKE especially preferably is the group

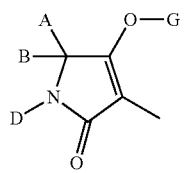

W especially preferably is hydrogen or methyl,
X especially preferably is chlorine or methyl,
Y especially preferably is hydrogen, chlorine, bromine or methyl,
Z especially preferably is hydrogen or the radical

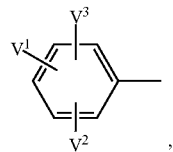

$V^1$ especially preferably is hydrogen, fluorine, chlorine, methyl, methoxy or trifluoromethyl, (emphasized for fluorine or chlorine in position 4),
$V^2$ especially preferably is hydrogen or fluorine in position 3,
$V^3$ especially preferably is hydrogen or fluorine in position 5,
A, B and the carbon atom to which they are bonded especially preferably are saturated $C_6$-cycloalkyl in which one ring member has been replaced by oxygen,
A, B and the carbon atom to which they are bonded especially preferably are saturated $C_6$-cycloalkyl which is substituted by a $C_4$-$C_5$-alkylenedioxyl group which with the carbon atom to which it is attached forms a 5-membered or 6-membered ring ketal, G especially preferably is hydrogen (a) or is one of the groups

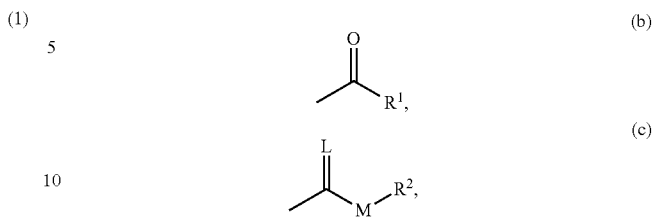

or E (f), (emphasized for groups (a) or (f))
in which
L is oxygen,
M is oxygen and
E is a metal ion equivalent or an ammonium ion, (emphasized for sodium or potassium)
$R^1$ especially preferably is in each case optionally singly fluorine- or chlorine-substituted $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or in each case optionally singly fluorine-, chlorine-, methyl- or methoxy-substituted cyclopropyl or cyclohexyl, or is optionally singly fluorine-, chlorine-, bromine-, cyano-, nitro-, methyl-, methoxy-, trifluoromethyl- or trifluoromethoxy-substituted phenyl,
$R^2$ especially preferably is in each case optionally singly fluorine-substituted $C_1$-$C_8$-alkyl, $C_2$-$C_6$-alkenyl or $C_1$-$C_4$-alkoxy-$C_2$-$C_3$-alkyl, phenyl or benzyl.

Preferred with emphasis are the compounds of the formula (I-1) with G=hydrogen

Unless indicated otherwise, optionally substituted radicals may be substituted one or more times, and in the case of multiple substitutions the substituents may be identical or different.

Mention may be made specifically, in addition to the compounds stated in the examples, of the following compounds of the formula (I-1-A) with G=hydrogen:

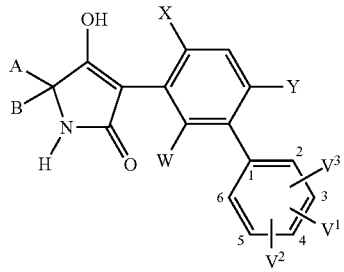

(I-1-A)

| Ex. No. | A | B | W | X | Y | $V^1$ | $V^2$ | $V^3$ | Known from WO 08/067911 |
|---|---|---|---|---|---|---|---|---|---|
| I-1-A-1 | —(CH$_2$)$_2$—O—(CH$_2$)$_2$— | | H | Cl | H | 4-F | H | H | I-1-a-13 |
| I-1-A-2 | —(CH$_2$)$_2$—O—(CH$_2$)$_2$— | | H | Cl | H | 4-F | 3-F | H | I-1-a-21 |
| I-1-A-3 | —(CH$_2$)$_2$—O—(CH$_2$)$_2$— | | H | Cl | H | 4-F | 3-F | 5-F | I-1-a-30 |
| I-1-A-4 | —(CH$_2$)$_2$—O—(CH$_2$)$_2$— | | H | CH$_3$ | H | 4-F | H | H | I-1-a-1 |
| I-1-A-5 | —(CH$_2$)$_2$—O—(CH$_2$)$_2$— | | H | CH$_3$ | H | 4-F | 3-F | H | I-1-a-3 |
| I-1-A-6 | —(CH$_2$)$_2$—O—(CH$_2$)$_2$— | | H | CH$_3$ | H | 4-F | 3-F | 5-F | I-1-a-28 |
| I-1-A-7 | —(CH$_2$)$_2$—O—(CH$_2$)$_2$— | | CH$_3$ | CH$_3$ | H | 4-F | H | H | I-1-a-4 |
| I-1-A-8 | —(CH$_2$)$_2$—O—(CH$_2$)$_2$— | | CH$_3$ | CH$_3$ | H | 4-F | 3-F | H | I-1-a-5 |
| I-1-A-9 | —(CH$_2$)$_2$—O—(CH$_2$)$_2$— | | CH$_3$ | CH$_3$ | H | 4-F | 3-F | 5-F | I-1-a-25 |
| I-1-A-10 | —(CH$_2$)$_2$—O—(CH$_2$)$_2$— | | H | CH$_3$ | H | 4-Cl | H | H | I-1-a-22 |
| I-1-A-11 | —(CH$_2$)$_2$—O—(CH$_2$)$_2$— | | CH$_3$ | CH$_3$ | H | 4-Cl | H | H | I-1-a-15 |

Mention may further be made specifically, as well as of the compounds stated in the examples, of the following compounds of the formula (I-1-B) where G and Z=hydrogen

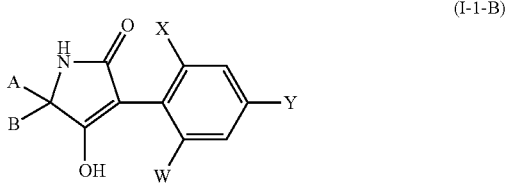

(I-1-B)

| Ex. No. | W | X | Y | A | B | Known from WO 06/089633; Ex. No. |
|---|---|---|---|---|---|---|
| I-1-B-1 | CH$_3$ | CH$_3$ | CH$_3$ | —(CH$_2$)$_2$—C—(CH$_2$)$_2$— O—(CH$_2$)$_2$—O | | I-1-a-2 |
| I-1-B-2 | CH$_3$ | CH$_3$ | Cl | —(CH$_2$)$_2$—C—(CH$_2$)$_2$— O—(CH$_2$)$_2$—O | | I-1-a-4 |
| I-1-B-3 | CH$_3$ | CH$_3$ | Br | —(CH$_2$)$_2$—C—(CH$_2$)$_2$— O—(CH$_2$)$_2$—O | | I-1-a-26 |
| I-1-B-4 | CH$_3$ | CH$_3$ | CH$_3$ | —(CH$_2$)$_2$—C—(CH$_2$)$_2$— O—(CH$_2$)$_3$—O | | I-1-a-18 |
| I-1-B-5 | CH$_3$ | CH$_3$ | Cl | —(CH$_2$)$_2$—C—(CH$_2$)$_2$— O—(CH$_2$)$_3$—O | | I-1-a-14 |
| I-1-B-6 | CH$_3$ | CH$_3$ | Br | —(CH$_2$)$_2$—C—(CH$_2$)$_2$— O—(CH$_2$)$_3$—O | | I-1-a-19 |

As already mentioned, the compounds which can be used in accordance with the invention can be employed outstandingly for the control of fish parasites and more particularly of fish-parasitizing crustaceans. They include the Copepodae (water fleas) with the following genera:
Achthares
Aegidae
Aegidae
Anilocridae
Anilocridae
Annelids
Basanistes
Benedenia
Brachiella
Branchiuran
Bromineolochiadae
Caligidae
Calijidae
Capsalids
Capsaloidea
Cecropidae
Ceudrolasus
Chondracanthidae
Cleidodiscus
Corallanidae
Cymothidae
Cymothids
Dactylogyroidea
Dermophthirius
Dichelestiidae
Dichelestinum
Elythrophora
Entobdellasolea
Epibrachiella
Ergasilidae
Flabellifera
Gnathiidae
Gyrodactyloidea
Gyrodactylus
Hatschekia
Isopod
Lamproglenz
Legosphilus
Lepeophtheirus
Lernaeacera
Lernaeenicus
Lemaeidae
Lemaeopidae
Monogenean
Monopisthocotylea
Monopisthocotylean
Myzobdella
Neobenedenia

*Olenicra*
*Opistolernaea*
*Pennella*
*Philichthyidae*
*Piscicola*
*Polypisthocotylea*
*Praniza*
*Pseudocaligus*
*Pseudocycmus*
*Pseudocycnidae*
*Pseudodactylogyrus*
*Pseudotracheliastes*
*Salmincola*
*Sphyriidae*
*Symphodus*

According to one preferred embodiment, the compounds which can be used in accordance with the invention are employed for the control of Caligidae (*Caligulus* spp.).

With particular preference, the compounds which can be used in accordance with the invention are employed for the control of *Lepeophtheirus* spp. such as, for example, *Lepeoptheirus salmonis*.

The fish include productive, farmed, aquarium and ornamental fish of all age stages, which live in fresh, salt or brackish water. The productive and farmed fish include for example
Atlantic salmon (*Salmo salar*)
Barramundi (*Lates calcarifer*)
Bighead carp (*Hypophthalmichthys nobilis*)
Bluefin Tuna
Catla (*Catla catla*)
Channel catfish (*Ictalurus punctatus*)
Cichlidae
Cobia (*Rachycentron canadum*)
Coho salmon (*Oncorhynchus kisutch*)
Common carp (*Cyprinus carpio*)
Cyprinid fish (*Cyprimidae*)
European eel (*Anguilla anguilla*)
European seabass (*Dicentrarchus labrax*)
Flathead grey mullet (*Mugil cephalus*)
Gilthead seabream (*Sparus aurata*)
Grass carp (*Ctenopharyngodon idellus*)
Japanese amberjack (*Seriola quinqueradiata*)
Japanese eel (*Anguilla japonica*)
Japanese kelp (*Laminaria japonica*)
Mandarin fish (*Siniperca chuatsi*)
Meagre (*Argyrosomus regius*)
Milkfish (*Chanos chanos*)
Mrigal carp (*Cirrhinus mrigala*)
Nile tilapia (*Oreochromis niloticus*)
Nori (*Porphyra* spp.)
Pangasius
Plagioscion
Pompano
Rainbow trout (*Oncorhynchus mykiss*)
Red drum (*Sciaenops ocellatus*)
Red swamp crawfish (*Procambarus clarkii*)
Roho labeo (*Labeo rohita*)
Amberjacks (*Seriola* spp.)
Siberian sturgeon (*Acipenser baerii*)
Silver carp (*Hypophthalmichthys molitrix*)
Striped catfish (*Pangasius hypophthalmus*)
Turbot (*Psetta maxima*)
Snakehead
Yellowfin Tuna The compositions of the invention are particularly suitable for the treatment of fish fry, e.g. carp 2 to 4 cm in body length.

The compositions are also highly suitable in eel fattening.

According to a further preferred embodiment, the compounds are used for the treatment of *Seriola* spp.

According to a further preferred embodiment, the compounds are used for the treatment of seabass (*Cicentrarchus labrax*).

According to a further particularly preferred embodiment, the compounds are used for the treatment of salmonid fish (Salmonidae).

The fish are treated either orally, via the feed, for example, or by bath treatment, an example being a "medical bath" into which the fish are put and in which they are kept for a certain period (minutes to several hours), for example when they are transferred from one rearing tank to the other. In special cases, treatment may also take place parenterally, by injection, for example.

The environment of the fish may also undergo transient or long-term treatment, for example in net cages, entire pond systems, aquariums, tanks or troughs in which the fish are kept.

The active ingredient is administered in preparations which are adapted to the applications.

Preparations for oral administration are powders, granules, solutions, emulsifiable concentrates or suspension concentrates, which as feed additives are mixed homogeneously with the feed or are applied to the surface of the feed.

Preparations for administration as a bath or for the treatment of the environment are powders, granules, solutions, emulsifiable or suspension concentrates, emulsions or suspensions, tablets or the active ingredient itself. The formulations can be administered by the user in dilute or neat form.

The preparations are produced in a conventional way, by subjecting the active ingredient to mixing, granulating, grinding and/or compacting or encapsulation with solid or soluble liquid carriers, optionally with addition of further auxiliaries such as emulsifiers or dispersants, solubilizers, dyes, antioxidants and/or preservatives.

In comparison to the customary compounds, ketoenols can generally be used at the application concentrations optionally also in undiluted form.

More convenient to handle, however, are products in which the active ingredient is present in a diluted form. Suitable diluents for fish and other marine animals and plants are non-toxic substances, which may be liquid or else solid, and water as well immediately prior to use in accordance with the invention.

Also suitable for practical use are film-like solids or capsules made of other gelatinous materials, containing the active ingredient in a readily water-soluble matrix, or film-like solids or capsules of other gelatinous materials from which the active ingredient diffuses out over the time of the application.

The active ingredient itself, its ground form or its solid formulations may be employed in water-soluble packaging, such as in polyvinyl alcohol pouches together with the closed pack. The user is no longer exposed to the active ingredient or its formulations.

Semi-solid application forms as well can be used for bath treatment. The active ingredient dissolved or suspended therein is leached from oily or fatty matrices. The release can be controlled through selection of the auxiliaries, the concentration of the active ingredient and the shape (surface); compresses or melts of hard fats containing the active ingredient are likewise suitable for the application.

The diluted compositions of the invention are prepared by contacting the active ingredient of the formula (I) with solid and/or liquid formulating auxiliaries, by progressive mixing and/or grinding, in such a way as to achieve an optimum development by the formulation of its anti-parasitic activity, in conformance with the application.

The formulating steps can be supplemented by kneading, granulating (granules) and optionally pressing, extruding or injection-moulding (pellets, tablets).

Formulating auxiliaries used are, for example, solid carriers which are non-toxic, for example, for the marine flora and fauna, and also solvents and optionally surface-active substances (surfactants).

The formulating auxiliaries below are used in preparing the compositions of the invention:

Solid carriers such as, for example, kaolin, talc, bentonite, sodium chloride, calcium phosphate, carbohydrates, cellulose powders, cottonseed meal, polyethylene glycol ethers, optionally binders such as, for example, gelatin, soluble cellulose derivatives, if necessary with addition of surface-active substances such as ionic or nonionic dispersants; additionally, natural, finely ground minerals such as calcite, montmorillonite or attapulgite. For improving the physical properties it is also possible to add highly disperse silica or highly disperse absorbent polymers. Suitable granulated, adsorptive granule carriers are porous types, such as, for example, pumice, crushed brick, sepiolite or bentonite, while suitable non-sorptive carrier materials are, for example, calcite or sand. It is possible, furthermore, to use a multiplicity of pregranulated materials of organic or inorganic nature, such as, more particularly, dolomite or comminuted plant material. Sorptive organic materials as well, such as polyacrylates, can be admixed with the active ingredient and employed.

Suitable solvents include the following: aromatic hydrocarbons, preferably the $C_8$-$C_{12}$ fractions, such as, for example, xylene mixtures or substituted naphthalenes, phthalic esters such as dibutyl or dioctyl phthalate; aliphatic hydrocarbons such as, for example, cyclohexane or paraffins, alcohols and glycols and also their ethers and esters, such as, for example, ethanol, ethylene glycol, ethylene glycol monomethyl or ethyl ether, ketones such as, for example, cyclohexanone, strongly polar solvents such as, for example, N-methyl-2-pyrrolidone, dimethyl sulphoxide or dimethylformamide, and also optionally epoxidized vegetable oils such as, for example, epoxidized coconut oil or soyabean oil and water.

Surface-active compounds contemplated, depending on the nature of the active ingredient of the formula (I) that is to be formulated, include nonionic, cationic and/or anionic surfactants having good emulsifying, dispersing and wetting properties. Surfactants are also understood to include surfactant mixtures.

Suitable anionic surfactants may be not only water-soluble soaps but also water-soluble synthetic surface-active compounds.

Soaps include the alkali metal salts, alkaline earth metal salts or optionally substituted ammonium salts of higher fatty acids ($C_{10}$-$C_{22}$), such as, for example, the Na or K salts of oleic or stearic acid, or of natural fatty acid mixtures which are obtainable, for example, from coconut oil or tallow oil.

Frequently use is made of so-called synthetic surfactants, more particularly fatty sulphonates, fatty sulphates, sulphonated benzimidazole derivates or alkylsulphonates.

The fatty sulphonates or fatty sulphates are generally in the form of alkali metal salts, alkaline earth metal salts or optionally substituted ammonium salts and have an alkyl radical having 8 to 22 C atoms, with alkyl also including the alkyl part of acyl radicals, an example being the Na salt or Ca salt of lignosulphonic acid, of dodecyl sulphate or of a fatty alcohol sulphate mixture prepared from natural fatty acids. Also included among these are the salts of the sulphuric esters and sulphonic acids of fatty alcohol-ethylene oxide adducts. The sulphonated benzimidazole derivatives contain preferably 2 sulphonic acid groups and a fatty acid radical having 8 to 22 C atoms. Alkylarylsulphonates are, for example, the Na, Ca or triethanolamine salts of dodecylbenzenesulphonic acid, of dibutylnaphthalenesulphonic acid or of a naphthalenesulphonic acid-formaldehyde condensation product.

Furthermore, it is also possible for corresponding phosphates to be employed, such as, for example, salts of the phosphoric ester of a p-nonylphenol-(4-14)ethylene oxide adduct, or phospholipids, as formulating auxiliaries.

Suitable nonionic surfactants include primarily polyglycol ether derivatives of aliphatic or cycloaliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkylphenols.

Further suitable nonionic surfactants are the water-soluble polyethylene oxide adducts, containing 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The stated compounds typically contain 1 to 5 ethylene glycol units per propylene glycol unit.

Examples that may be mentioned of nonionic surfactants include nonylphenolpolyethoxyethanols, castor oil polyglycol ethers, polypropylene-polyethyleneoxy adducts, tributylphenoxypolyethoxyethanol, polyethylene glycol and octylphenoxypolyethoxyethanol.

Also contemplated, furthermore, are fatty acid esters of polyoxyethylenesorbitan, such as polyoxyethylenesorbitan trioleate.

The cationic surfactants are quaternary ammonium salts which as N substituent(s) comprise at least one alkyl radical having 8 to 22 C atoms and as further substituents comprise lower, optionally halogenated alkyl, benzyl or lower hydroxyalkyl radicals. The salts preferably take the form of halides, methylsulphates or ethylsulphates, an example being stearyltrimethylammonium chloride or benzyldi(2-chloroethyl)ethylammonium bromide.

The surfactants that are customary in formulation technology are described in publications including the following:

"McCutcheon's Detergents and Emulsifiers Annual" MC Publishing Corp., New Jersey, 1990; Helmut Stache "Tensid-Taschenbuch" Carl Hanser-Verlag Munich/Vienna 1981.

Suitable binders for water-soluble granules or tablets include chemically modified, polymeric natural substances that are soluble in water or in alcohol, such as starch derivatives, cellulose derivatives or protein derivatives (e.g. methylcellulose, carboxymethylcellulose, ethylhydroxyethylcellulose, proteins such as zein, gelatin and the like) and also synthetic polymers such as, for example, polyvinyl alcohol, polyvinylpyrrolidone etc. Tablets further comprise fillers (e.g. starch, microcrystalline cellulose, sugars, lactose, etc.), lubricants and disintegrants.

Bath application of the compositions of the invention to the parasites that are to be controlled can be carried out by adding the compositions in the form of solutions, emulsions, suspensions, powders or tablets to the cage, where they are rapidly dissolved and dispersed by the movement of the fish and by the water running through. Concentrated solutions may also be diluted with relatively large volumes of water before being added to the cages. Concentration problems in the cages do not generally occur, since the fish respond to any opening of the cages, in expectation of feed, by wild inter-agitation, ensuring rapid dilution.

The anti-parasitic compositions of the invention comprise generally 0.1% to 99%, more particularly 0.1% to 95%, by weight of active ingredient of the formula (I), and 99.9% to 1%, more particularly 99.9% to 5%, by weight of a solid or liquid additive, including 0% to 25%, more particularly 0.1% to 25%, by weight of a surfactant.

While the commercial product tends preferably to be concentrated compositions, the end user generally employs diluted compositions, which he or she obtains by diluting the commercial product with water.

Such compositions may further comprise additional adjuvants such as stabilizers, defoamers, viscosity regulators, binders, stickers and other active ingredients for the purpose of obtaining specific effects.

The concentration of the active ingredient on application is dependent on the nature and duration of the treatment and also on the age and condition of the fish being treated. In the case of short-term treatment, for example, it is 0.1 to 100 mg of active ingredient per litre of water, preferably 0.5 to 10 mg per litre, for a treatment time of 0.3 to 4 hours.

In the case of pond treatments, 0.01 to 50 mg of active ingredient may be used per litre of water.

The composition of preparations for use as feed additive is for example as follows:

| a) | Active ingredient of the formula (I) | 1-10 parts by weight |
| | Soyabean protein | 49-90 parts by weight |
| | Finely ground lime | 0-50 parts by weight |
| b) | Active ingredient of the formula (I) | 0.5-10 parts by weight |
| | Benzyl alcohol | 0.08-1.4 parts by weight |
| | Hydroxypropylmethylcellulose | 0-3.5 parts by weight |
| | Water | Remainder to 100 |

Preparations for bath application are, for example, the following solutions, emulsifiable concentrates or suspension concentrates.

| c) | Active ingredient of the formula (I) | 5.0% |
| | Anionic emulsifier | 10.0% |
| | N-Methylpyrrolidone | 25.0% |
| | Mineral oil | 60.0% |
| d) | Active ingredient of the formula (I) | 25.0% |
| | Anionic emulsifier | 8.0% |
| | Nonionic emulsifier | 2.0% |
| | Dimethyl sulphoxide | 35.0% |
| | N-Methylpyrrolidone | 30.0% |
| e) | Active ingredient of the formula (I) | 30.0% |
| | Urea | 10.0% |
| | Polyvinyl alcohol | 0.5% |
| | Gum (e.g. xanthan gum) | 0.4% |
| | Preservative | 0.1% |
| | Water | 49.0% |

A Biological Example: Control of Salmon Louse in Salmon

Four groups each of 40 salmon were infected per fish with about 15 *Lepeoptheirus salmonis* at the "copepodid stage" of development. Two groups received medicated feed containing the compound of Example I-1-A-7 or the compound of Example I-1-B-2 as active ingredient. The feed was administered daily in a quantity of about 0.8% of the body weight, divided up into three portions over the day. The medicated feed supplied the salmon with the active ingredients at a dose of 2.5 mg per kg of body weight per day.

The control groups received unmedicated feed.

As shown by the results in the table below, salmon louse infestation was effectively controlled with both active ingredients.

| | Day 0 | Day 7 | Day 21 |
|---|---|---|---|
| Salmon lice per fish (average) I-1-A-7 | 15 | 1.2 | 0.1 |
| Salmon lice per fish (average) I-1-B-2 | 15 | 1.1 | 0.1 |
| Control group 1 | 15 | 4.6 | 1 |
| Control group 2 | 15 | 6.4 | 0.8 |

The invention claimed is:

1. A method of controlling parasitic Copepodae comprising administering to a fish a compound of the formula (I)

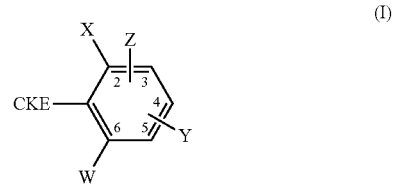

in which

W is hydrogen, alkyl, halogen, haloalkyl, alkoxy or haloalkoxy,

X is alkyl, alkenyl, alkynyl, halogen, alkoxy, haloalkyl, haloalkoxy or cyano,

Y is hydrogen, alkyl, alkoxy or halogen,

Z is hydrogen, halogen, alkyl, alkoxy, haloalkyl, haloalkoxy or optionally singly or multiply substituted phenyl, CKE is one of the groups

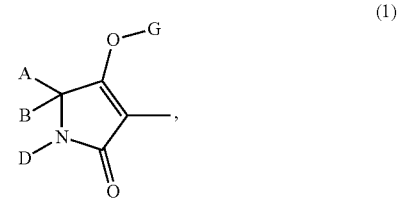

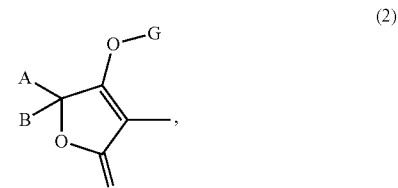

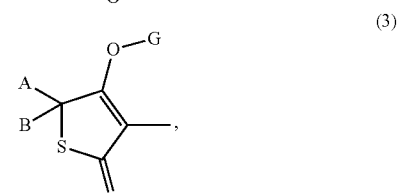

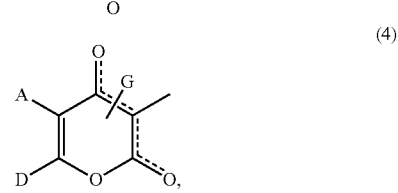

(5) 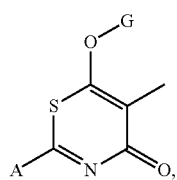

(6) 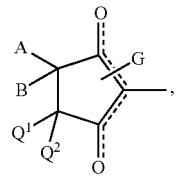

(7) 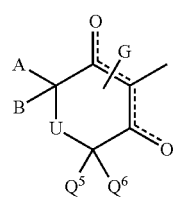

(8) 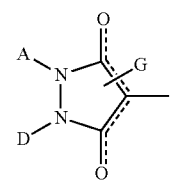

(9) 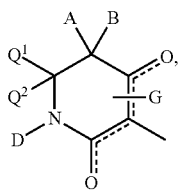

(10) or

(11) 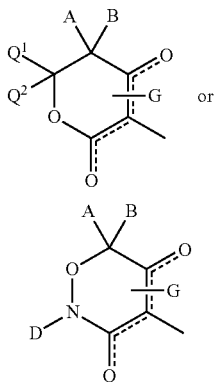

in which
U is —S—, —S(O)—, —S(O)$_2$—, —O—,

or an S=N—, S(O)=N— or

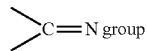

or is optionally Q$^3$ and Q$^4$-substituted C$_1$-C$_4$-alkylene which may optionally be interrupted by oxygen, A is hydrogen, or is in each case optionally halogen-substituted alkyl, alkenyl, alkoxyalkyl, alkylthioalkyl, saturated or unsaturated, optionally substituted cycloalkyl, in which optionally at least one ring atom has been replaced by a heteroatom, or is in each case optionally halogen-, alkyl-, haloalkyl-, alkoxy-, haloalkoxy-, cyano- or nitro-substituted aryl, arylalkyl or hetaryl, B is hydrogen, alkyl or alkoxyalkyl, or A and B together with the carbon atom to which they are attached are a saturated or unsaturated, unsubstituted or substituted ring system optionally containing at least one heteroatom, D is hydrogen or an optionally substituted radical from the series alkyl, alkenyl, alkynyl, alkoxyalkyl, saturated or unsaturated cycloalkyl, in which optionally one or more ring members have been replaced by heteroatoms, or is in each case optionally substituted arylalkyl, aryl, hetarylalkyl or hetaryl, or A and D together with the atoms to which they are attached are a saturated or unsaturated ring system which optionally contains at least one (when CKE=8 and 11 one further) heteroatom and which is unsubstituted or substituted in the A,D moiety, or A and Q$^1$ together are in each case optionally substituted alkanediyl or alkenediyl which may optionally be interrupted by at least one heteroatom, an

or substituted

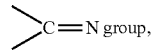

or,

B and Q$^2$ together with the atoms to which they are attached are a saturated or unsaturated ring system which optionally contains at least one heteroatom and which is unsubstituted or substituted in the B, Q$^2$ moiety, or D and Q$^1$ together with the atoms to which they are attached are a saturated or unsaturated ring system which optionally contains at least one heteroatom and which is unsubstituted or substituted in the D, Q$^1$ moiety, Q$^1$ is hydrogen, alkyl, alkoxyalkyl, optionally substituted cycloalkyl, in which optionally a methylene group has been replaced by oxygen or sulphur, or is optionally substituted phenyl, Q$^2$, Q$^4$, Q$^5$ and Q$^6$ independently of one another are hydrogen or alkyl, Q$^3$ is hydrogen, or is in each case optionally substituted alkyl, alkoxy, alkylthio, alkoxyalkyl, alkylthioalkyl, optionally substituted cycloalkyl, in which optionally one or two methylene groups have been replaced by oxygen or sulphur, or is optionally substituted phenyl, or Q$^1$ and Q$^2$ together with the carbon atom to which they are attached are an unsubstituted or substituted ring system optionally comprising a heteroatom, or Q$^3$ and Q$^4$ together with the carbon atom to which they are attached are a saturated or unsaturated, unsubstituted or substituted ring system optionally comprising at least one heteroatom, or A and $Q^3$ together with the carbon atom to which they are attached are a saturated or unsaturated, unsubstituted or substituted ring system optionally comprising at least one heteroatom, or A and $Q^5$ together with the carbon atom to which they are attached are a saturated or unsaturated, unsubstituted or substituted ring system optionally comprising at least one heteroatom, G is hydrogen (a) or is one of the groups

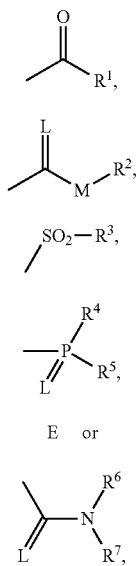

(b)

(c)

(d)

(e)

(f)

(g)

in which

E is a metal ion equivalent or an ammonium ion,

L is oxygen or sulphur,

M is oxygen or sulphur, $R^1$ is in each case optionally halogen-substituted alkyl, alkenyl, alkoxyalkyl, alkylthioalkyl, polyalkoxyalkyl, or is optionally halogen-, alkyl- or alkoxy-substituted cycloalkyl, which may be interrupted by at least one heteroatom, or is in each case optionally substituted phenyl, phenylalkyl, hetaryl, phenoxyalkyl or hetaryloxyalkyl, $R^2$ is in each case optionally halogen-substituted alkyl, alkenyl, alkoxyalkyl, polyalkoxyalkyl, or is in each case optionally substituted cycloalkyl, phenyl or benzyl, $R^3$, $R^4$ and $R^5$ independently of one another are in each case optionally halogen-substituted alkyl, alkoxy, alkylamino, dialkylamino, alkylthio, alkenylthio, cycloalkylthio or are in each case optionally substituted phenyl, benzyl, phenoxy or phenylthio, $R^6$ and $R^7$ independently of one another are hydrogen, or are in each case optionally halogen-substituted alkyl, cycloalkyl, alkenyl, alkoxy, alkoxyalkyl, or are optionally substituted phenyl, or are optionally substituted benzyl, or together with the N atom to which they are bonded are a ring system optionally interrupted by oxygen or sulphur.

2. The method according to claim 1, wherein the parasitic Copepodae are from the genus *Caligidae*.

3. The method according to claim 1, wherein the parasitic Copepodae are from the genus *Lepeophtheirus*.

4. The method according to claim 3, wherein the parasitic Copepodae is *Lepeoptheirus salmonis*.

5. The method according to claim 1, wherein the fish is a salmonid fish (*Salmonidae*).

6. The method according to claim 1, wherein the fish is a carp.

7. The method according to claim 1, wherein the fish is a seabass (*Dicentrarchus labrax*).

8. The method according to claim 1, wherein the fish is an amberjack (*Seriola* spp.).

9. The method according to claim 4, wherein the fish is a salmonid fish (*Salmonidae*).

10. The method according to claim 4, wherein the fish is a carp.

11. The method according to claim 4, wherein the fish is a seabass (*Dicentrarchus labrax*).

12. The method according to claim 4, wherein the fish is an amberjack (*Seriola* spp.).

* * * * *